United States Patent [19]
Francis et al.

[11] Patent Number: 5,256,784
[45] Date of Patent: Oct. 26, 1993

[54] NONLINEAPHORES AND POLYMERS INCORPORATING SUCH NONLINEAPHORES

[75] Inventors: Cecil V. Francis, Woodbury; Elisa M. Cross, St. Paul; Roberta E. Harelstad, Bloomington; Paul F. Korkowski, Hastings; Peter C. Leung, Woodbury; David W. Macomber, St. Paul; John E. Trend, St. Paul, all of Minn.

[73] Assignee: Minnesota Mining and Manufacturing Company, St. Paul, Minn.

[21] Appl. No.: 822,168

[22] Filed: Jan. 16, 1992

[51] Int. Cl.$^5$ .................. C09B 62/245; C09B 23/04; C09B 23/02; C09B 23/06
[52] U.S. Cl. .................. 544/294; 544/311; 546/174; 548/184; 548/244; 560/354; 560/358; 564/48; 564/50; 359/321; 359/326; 534/789; 385/141
[58] Field of Search .............. 544/294, 311; 546/174; 548/184, 244; 560/354, 358; 564/48, 50

[56] References Cited

U.S. PATENT DOCUMENTS

| | | | |
|---|---|---|---|
| Re. 28,208 | 10/1974 | Sato et al. | 546/174 X |
| 2,185,343 | 1/1940 | Keyes et al. | 546/174 X |
| 2,748,114 | 5/1956 | Brooker et al. | 546/174 X |
| 2,935,393 | 5/1960 | Luckenbaugh | 564/48 X |
| 2,956,881 | 10/1960 | Van Lare | 96/102 |
| 3,160,648 | 12/1964 | O'Brochta et al. | 560/354 |
| 3,395,329 | 7/1968 | Rentzepis | 321/69 |
| 3,420,787 | 1/1969 | Reymore et al. | 564/48 X |
| 3,431,484 | 3/1969 | Pao et al. | 321/69 |
| 3,555,071 | 11/1970 | Rao et al. | 564/48 X |
| 3,702,767 | 11/1972 | Ohlschlager et al. | 546/174 X |
| 3,718,692 | 2/1973 | Rao et al. | 560/358 |
| 3,758,465 | 9/1973 | Jenkins | 546/174 X |
| 3,858,124 | 12/1974 | Bass et al. | 332/0.51 |
| 4,166,740 | 9/1979 | Webster | 96/1 PE |
| 4,796,971 | 1/1989 | Robello et al. | 350/96.34 |
| 4,810,338 | 3/1989 | DeMartino et al. | 204/157.88 |
| 4,886,339 | 12/1989 | Scozzafava et al. | 350/96.34 |
| 5,001,209 | 3/1991 | Wreesmann et al. | 528/70 |

FOREIGN PATENT DOCUMENTS

| | | | |
|---|---|---|---|
| 0350112A1 | 10/1990 | European Pat. Off. | 528/70 |
| 0445854A1 | 11/1991 | European Pat. Off. | 523/119 |
| 0445864A1 | 11/1991 | European Pat. Off. | 350/96.34 |
| 2-179624 | 7/1990 | Japan | 96/102 |

OTHER PUBLICATIONS

SPIE vol. 1147, Nonlinear Optical Properties of Organic Materials II, pp. 48–60 (1989) (Leung et al).
The Journal of Chemical Physics, vol. 66, No. 5, (Mar. 1977) pp. 2664–2668 (Oudar et al.).
Journal of Polymer Science: Part A: Polymer Chemistry, vol. 27, 1515–1524 (1989) (Katritzky et al.).
The Preparation of the Halogenophenylacetic Acids, J. Chem. Soc. (London), Campbell et al., vol. 1948, pp. 1251–1255 (Sep. 1947).
Preparation of Rhodanine Derivatives as Possible Anthelmintics, J. Chem. Soc. (London), Mackie et al, vol. 1954, pp. 3919–3922 (Jul. 1954).
0740-3224/91/040887-08, Journal of the Optical Society of America B, "Second-harmonic generation as a probe of rotational mobility in poled polymers", vol. 8, No. 4 (Apr. 1991) Boyd et al., pp. 887–894.
"Synthesis and study of the mesomorphism of highly (List continued on next page.)

Primary Examiner—Floyd D. Higel
Attorney, Agent, or Firm—Gary L. Griswold; Walter N. Kirn; Carolyn V. Peters

[57] ABSTRACT

Nonlinear-optic (NLO) compositions containing functionalized merocyanine dyes, such that the molecules, comprising the NLO-active compositions have a functional group at each end of the molecule and each functional group differing in reactivity, thus permitting stepwise reaction of each functional group, and NLO-active molecules prepared from hemioxonol dyes derviatived with (meth)acrylate or (meth)acrylamide groups, and their uses in devices such as second harmonic generators or polymer integrated optics.

23 Claims, No Drawings

OTHER PUBLICATIONS polarizable mesogens towards applications in non-linear optics", Liquid Crystals, vol. 2, No. 1, pp. 55-61, (1987) Tournilhac et al.

"Communications to the Editor", Journal of the American Chemical Society, 94:17, pp. 6190-6191, (Aug. 1972) (Corey et al.).

"Organic Syntheses", Collective vol. 2, p. 60 Dickey et al. (1943).

"Urethane Chemistry and Applications", ACS Symposium Series 172, 0097-6156/81/0172-0205, American Chemical Society 1981 (Huynh-Ba et al.) pp. 205-217.

"Principles of Polymerization" 2nd Ed., George Odian, Table of Contents (1985) pp. XI-XXVI.

"Encyclopedia of Chemical Technology", vol. 21, Kirk-Othmer, p. 494 (1970).

"Chemistry Letters", The Chemical Society of Japan, pp. 1803-1806, (1989) Ikeda et al.

0897-4756/90/2802-0229, Chem. Mater., American Chemical Society, vol. 2, pp. 229-231, (1990) Park et al.

0021-8979/89/193241-07, J. Appl. Phys. 66 (7), pp. 3241-3247, (Oct. 1989) Eich et al.

0003-6951/88/131031-03, Appl. Phys. Lett. 52 (13), pp. 1031-1033, (Mar. 1988) Thackara et al.

The Journal of Chemical Physics, vol. 63, No. 6, pp. 2666-2682 (Sep. 1975) Levine et al.

Huthig & Wepf Verlag, Basel, CCC 0025-116X/91, (1991) pp. 1009-1016 Mandal et al.

"Nonlinear Optical Properties of Organic and Polymeric Materials", ACS Symposium Series 233, American Chemical Society (1983) p. VII.

"Nonlinear Optical Properties of Organic Materials II", SPIE-The International Society for Optical Engineering, vol. 1147, (Aug. 1989) pp. III to V.

Communication No. 1396 From the Kodak Research Laboratories, vol. 73, pp. 5326-5358 (1951) Brooker et al.

Mol. Cryst. Liq. Cryst., vol. 189, pp. 93-106 (1990) Dai et al.

"Colour and Constitution of Organic Molecules", John Griffiths, Academic Press, pp. 147-147 (1976).

Angew. Chem. 96 pp. 637-651, (1984) 0044-8249/84/0909-0637 Williams.

Proc. SPIE-Int'l. Soc'y Opt. Eng., vol. 1213, Photopolym. Devic Phys., Chem. Appl. (1990), Man et al. pp. 7 to 16.

NONLINEAPHORES AND POLYMERS INCORPORATING SUCH NONLINEAPHORES

BACKGROUND OF THE INVENTION

1. Field of the Invention

This invention relates to merocyanine dyes comprising rhodanine, barbituric acid, thiobarbituric acid, and isoxazolone groups, condensation polymers and (meth-)acrylated polymers incorporating such dyes, the dyes and polymers being useful in nonlinear-optical applications.

2. Description of the Related Art

Several polymers have been reported in the literature for use as active nonlinear-optical (NLO) compositions, see for example *Nonlinear-optical Properties of Organic Material* 1147 (Khanarian, G., ed., SPIE Proc., San Diego, 1989). Most of them are linear polymers bearing NLO-active groups (hereinafter for brevity referred to as "nonlineaphores") as side chains, in which the aligned dipoles tend to relax over extended periods of time at room temperature or slightly elevated temperatures. Some of the noted exceptions are the acrylates/methacrylates reported by Man et al. *Proc. SPIE-Intl. Soc'y Opt. Eng.* 1213 (Photopolym. Device Phys., Chem., Appl., 1990); and polyurethanes reported in U.S. Pat. No. 5,001,209 (Wreesman et al.). These polymers have glass transition temperatures ($T_g$), above 135° C. and are reported to be stable at elevated temperatures.

Recently, an increasing number of publications have appeared in which the issue of elevated temperature stability is being addressed by use of cross-linked polymers. These polymers can be divided into two classes, namely, those cross-linked around the NLO units, to restrict the free volume available for relaxation of the NLO moiety, and those cross-linked through the NLO units, to covalently bind the NLO moiety of the NLO unit at more than one point.

U.S. Pat. No. 4,886,339 (Scozzafava et al.) describes one example of the former case. The disadvantage of this system is that a binder is needed to make a film of the monomer prior to poling/cross-linking and the reaction has to be carried out in an inert atmosphere. Furthermore, there is no guarantee that the resulting polymer will have a high enough cross-link density to prevent all rotation of the dipoles since the molecule is covalently bound only at one point. As reported by Park et al. *Chem. Mater.* 2 229 (1990), this type of cross-linking does provide some enhanced stability of the NLO moiety over versions that are not cross-linked but long term relaxation is still a problem.

Eich et al. *J. Appl. Phys.* 66 3241 (1989), have addressed the relaxation problem by utilizing epoxide chemistry to produce stable systems in which the NLO units are covalently held at more than one point. They report stability up to 85° C. for a film corona-poled at 140° C. for 16 hours. A possible problem of this system, apart from the long curing time required, is the long-term dimensional instability of the polymer film, especially in high humidity, since amine cured epoxides are known to have an affinity for water.

The phenomenon of molecular hyperpolarizability and related NLO effects are described in ACS Symposium Series 233, Am. Chem. Soc'y, (Washington, D.C. 1983). Generally, hyperpolarizable molecules have a delocalized pi ($\pi$)-electron system in which an electron donor group and an electron acceptor group are conjugatively coupled directly by a $\pi$-electron system. Molecules possessing large molecular hyperpolarizability are capable of ready polar orientation in an electric field. As a result, the affected material also becomes macroscopically hyperpolarizable. Such a material may be used in an optical switch in which the material is dispersed in a polymer host and an electric field is applied to the hyperpolarizable polymer. Such a use is described by Thackera *Appl. Phys. Lett.* 52 1031 (1988).

Heterocyclic dyes containing a hemioxonol nucleus were disclosed in U.S. Pat. No. 2,956,881 (Herold et al.). These dyes were used to alter the sensitivity of photographic emulsions.

More recently, Japanese Patent No. JP 2,179,624 (Ikeda et al.) discloses straight chain polyene compounds (general structure shown below) utilizing hemioxonol-based electron acceptor groups in NLO applications;

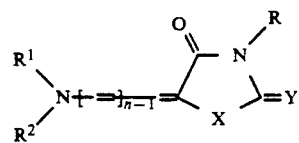

wherein R, $R^1$ and $R^2$ are independently a $C_{1-3}$ alkyl group, or $R^1$ and $R^2$ taken together form a $C_{4-6}$ polymethylene group or —$CH_2CH_2OCH_2CH_2$—; X is a heteroatom, wherein such heteroatom is selected from the group consisting of O, Si, Se, or X is $NC(O)R^3$, wherein $R^3$ is a $C_{1-3}$ alkyl group; Y is a heteroatom, wherein such heteroatom is selected from the group consisting of O, S, or Se; and n is an integer of 1 to 4.

The compounds described in JP 2,179,624 (Ikeda et al.), though they may possess large molecular hyperpolarizability, would be susceptible to chemical degradations, such as photochemical degradation or oxidation. The alternating double bonds in the polyenes tend to undergo oxidation similar to the known oxidation of retinol (Vitamin A) and its derivatives, see for example, Kirk-Othmer *Encycl. Chem. Technol* 21 494 (2 ed.).

Ikeda et al. *Chem. Lett.* 1803 (1989), have disclosed the use of dyes based on barbituric acid, hydantoin and rhodanine as small molecules with large second order hyperpolarizabilities. However, no mention is made of how to derivatize these molecules for polymer synthesis, thereby enabling incorporation of these molecules into either linear or cross-linked polymers. Furthermore, no mention is made of how to proces these materials into thermally stable, optically clear NLO polymeric films.

Mandal et al. *Makrom. Chem. Rapid Commun.* 12 63 (1991) have also described a photo-crosslinked material for NLO. In this material, the cross-links are formed by photo-dimerization of cinnamoyl groups. Drawbacks of the system are that only a modest concentration of NLO nonlineaphores ($\sim 20\%$) was achieved, and the reported second harmonic generation (SHG) temperature stability is limited to 65° to 80° C.

Cross-linked sulfone acrylates and methacrylates have been described in U.S. Pat. No. 4,796,971 (Robella et al.). However, the examples describe synthesis of materials in which the nonlineaphore is bound to the polymer network at only one end of the extended $\pi$-electron system. The NLO molecule is covalently bonded to the polymer at one point of attachment. As reported by Park et al., supra, this type of cross-linking does provide some enhanced stability of the NLO moiety over uncross-linked versions, but long term relaxation is still a problem. The material that was poled was a neat, functionalized nonlineaphore, or a mixture of functionalized nonlineaphore and a polymer binder. The polymer binder increased the viscosity of solutions, allowing thicker films to be produced, and improved the optical quality of the films by reducing the crystallization of the NLO component. However, the presence of the polymer binder reduced the nonlineaphore density in the final NLO material.

European Patent Application 0 445 854 A1 (van der Horst et al.) describes a thermally curable system containing donor conjugated π-electron acceptor (DπA) groups that can be poled by an electrical field while, simultaneously, the system is cured. The disclosed material comprised a DπA group containing compound (A) having two or more functional groups and a compound (B) having two or more functional groups reactive towards (A). One of the components (A) or (B) contained isocyanate groups. To obtain a polymeric network, at least one of the components (A) or (B) should be tri-functional or higher. The NLO molecule is covalently bonded at one point of attachment. As reported by Park et al., supra, this type of cross-linking does provide some enhanced instability of the NLO moiety over uncross-linked versions, but long term relaxation is still a problem.

As reported by Dai et al. *Materials for Nonlinear Optics*, ACS Symposium Series 455 pp 226–49 (Marder et al. ed 1991), NLO-active molecules can have functionality at both the donor and acceptor ends. The below-illustrated molecule was combined with epoxides to make crosslinked NLO polymers. The disadvantage of this type of functionality, that is, two identical groups, is that attachement of the nonlineaphore to the matric and crosslinking occur in the same step. Therefore, the prepolymerization step used to allow film formation (or avoid dielectric breakdown) would result in immobilization of some nonlineaphores in random configurations. Also, high nonlinaphore concentrations were not achieved in this system.

SUMMARY OF THE DISCLOSURE

Briefly, in one aspect of the present invention, nonlinear-optic compositions are provided, wherein the nonlinear-optic components are functionalized merocyanine dyes prepared from rhodanine, isoxazolone, barbituric acid, or thiobarbituric acid and having functionality at both ends, preferably having a reactivity of the functionality at the donor end different that the reactivity of the functionality at the acceptor end and can be described by the general formula: wherein

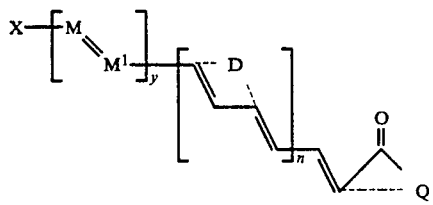

X is

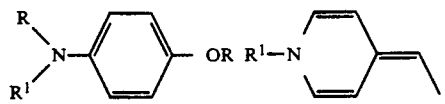

R and $R^1$ are independently an alkyl group or an alkyl group bearing a group having an active hydrogen, having 1 to 10 carbon atoms, preferably 1 to 6 carbon atoms, or R and $R^1$ taken together with a nitrogen atom form a heterocyclic nucleus containing five or six atoms in the heterocyclic ring bearing a group bearing an active hydrogen, examples of said nucleus being, 2-pyrrolidinomethanol, and 4-2-hydroxyethyl)piperazine;

y is 0 to 2;

M and $M^1$ are independently an olefinic carbon atom or a nitrogen atom, preferably M and $M^1$ are both olefinic carbon atoms;

D represents the atoms necessary to complete a cycloalkene ring preferably a 5- or 6-membered ring, wherein the atoms are carbon, and nitrogen, oxygen, or sulfur;

n is 0 or 1; and

Q represents the non-metallic atoms necessary to complete a nucleus of the indandione series, for example 1,3-diketohydrindene, or an unsaturated heterocyclic nucleus containing five or six atoms in its ring, such as those of the isoxazolone series, for example, 3-1'-(2'-hydroxy-2'-phenylethyl)-5-isoxazolone, etc.), those of the 2,4,6-triketohexahydropyrimidine series, for example, barbituric acid or 4,60dihydroxy-2-mercaptopyrimidine (hereinafter for brevity known as "2-thiobarbituric acid") as well as their derivatives containing groups bearing active hydrogens, and/or substituted and N-attached phenyl, fluorenyl, or stilbenyl groups where the substituents are electron withdrawing groups such as nitro, trifluoromethyl, or cyano, those of the 2-thio-4-thiazolidinone (rhodanine) series, for example, 3-aminorhodanine, 3-rhodanine acetic acid; and in general a heterocyclic nucleus containing 5 or 6 atoms in the heterocyclic ring and having at leat two heteroatoms, such heteroatoms being selected from the group consisting of a nitrogen atom, an oxygen atom, and a sulfur atom, preferably at least one of the heteroatoms being a nitrogen atom.

Depending on the conditions and the starting materials, functionalized merocyanine dye derivatives can be separated into several subclasses of derivatives. The functionalized derivatives are stable intermediates and may be prepared and stored for a period of time prior to further processing or use in NLO applications.

A first subclass comprises derivatives of merocyanine dyes wherein the derivatives have more than one functionality, that is, a functional group at each end of the molecule. Preferably, the functionalities differ in their reactivities, thus permitting stepwise reaction of each functionality. Advantageously, a soluble polymer or prepolymer is initially synthesized, and is processed into an optically clear, stable film. This film is then poled and subsequently cross-linked upon heating. The degree of cross-linking is dependent upon, inter alia, the poling temperature and the length of time the film is held at the poling temperature.

A second subclass of the present invention comprises NLO-active compounds prepared from merocyanine dyes derivatized with (meth)acrylic groups, including acrylic and methacrylic groups and specifically amides and esters. The functionalized derivative bears (meth)acrylate or (meth)acrylamide functionality at both ends of the compound, that is, a donor end and an acceptor end. Optionally, the NLO-active compounds can be incorporated into the backbone of linear polymers. The resulting polymer is then used as a polymeric binder or film former. The NLO compounds have a large optical nonlinearity and at least one polymerizable functionality at each end of the extended donor-π-acceptor system of the functionalized derivative. Attachment of both donor and acceptor ends of the compound within the network thus (providing cross-linking) severely decreases the mobility of the molecules and leads to increased SHG stability. Polymerization may be thermally or photochemically initiated under poling conditions, depending on the polymerization initiation conditions selected.

A third subclass of the functionalized derivatives of the present invention comprises derivatives prepared from merocyanine dyes wherein there is functionality at both ends of the donor-π-acceptor system and preferably the donor end is mono- or difunctional and the acceptor end bears a (meth)acrylate or (meth)acrylamide group. Such derivatives can be further processed into linear polymers and can be cross-linked under poling conditions and are NLO-active.

A fourth subclass of the functionalized derivatives of the present invention comprises derivatives prepared from merocyanine dyes wherein there is a hydroxyl group at the one end and a free or esterified carboxyl group at the other end. This subclass of derivatives can be heated to cause condensative melt-polymerization under poling conditions. Although the derivatives are not cross-linked, unlike the members of the other three subclasses, they too are NLO-active.

Advantageously, the first three subclasses are efficiently prepared and manufactured and provide improved stability. The fourth subclass, an NLO-active polymeric binder, is especially useful, for example, as a thickening polymer capable of providing increased NLO activity along with its primary function of thickening an NLO-active solution.

Advantageously, the NLO-active compositions of the present invention have a high nonlineaphore density, thus exhibiting high NLO activity, and solutions of the compositions are stable, thus retaining a long shelf life. The coated NLO-active compositions are stable at high temperatures and provide optically clear films.

Advantageously, the nonlineaphores of the present invention have different functionality at both the acceptor end and the donor end of the molecule. Having the functionalities with different reactivities allows stepwise reaction of the nonlineaphore ends. For example, in one of the systems described in the present invention, room temperature reaction of a nonlineaphore having both a hydroxy and an amino functionality with a multifunctional isocyanate results mainly in the reaction of the amino group. This covalent attachment of the nonlineaphore to the isocyanate matric allows the solution to be processed into an optically clear film of high nonlineaphore concentration. Since, the nonlinearphores are attached to the isocyanate at only one point, a higher degree of alignment may be possible than with the system described in Dai et al. supra. Simultaneous poling and heating of the film causes reaction of the hydroxy groups, leading to a highly crosslinked, optically clear NLO-active polymer of high nonlineaphore concentration.

The NLO-active compositions of the present invention are useful in second harmonic generators, or polymeric integrated optics, such as described in Lytel "Applications of Electro-optic Polymers to Integrated Optics, " *Nonlinear-Optical Materials and Devices for Photonic Switching* 30 1216 (1990).

In this application:

"processable" means being able to manipulate the material, for example, to form a film, whether by solvent casting or hot pressing; and "extended conjugated system" means coupling of parts of the molecule through delocalized electrons over alternating single and double bonds; and "optically transparent" means transparent or light transmitting with respect to incident fundamental light frequencies and, as required, harmonic light frequencies; and "nonlineaphore" means NLO-active groups or portions of molecules, or compounds; and "external field" means a substantially uni-directional electric field that is applied to a substrate of mobile organic molecules or groups, to induce dipolar alignment of the molecules or groups parallel to the field; and "second order" means any optical or electro-optical process that is dependent on the square of the magnitude of electric or optical fields. This includes second harmonic generation (SHG) wherein the frequency of light is doubled, three-wave mixing, Pockels effects, and the like; and "merocyanine" means one of a series of neutral donor-acceptor dyes having a general structure containing a donor group and an acceptor group connected by a chain of conjugated double bonds, wherein the chain of conjugated double bonds can contain one or more nitrogen atoms, J. Griffiths *Colour and Constitution of Organic Molecules* pp 146–7(1976)); and "poling" means orienting the dipole vectors of the molecule in the direction of the external field.

Functionalized merocyanine dyes are prepared by reacting a functionalized aldehyde with functionalized base acceptor derivatives based on rhodanine, isoxazolone (the "R" group can be any aliphatic or aromatic group), barbituric acid, or thiobarbituric acid structural units as described in the following formulas:

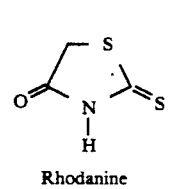
Rhodanine

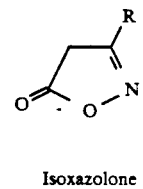
Isoxazolone

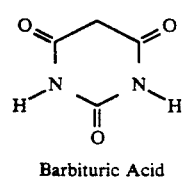
Barbituric Acid

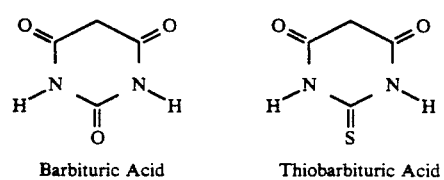
Thiobarbituric Acid

DESCRIPTION OF THE PREFERRED EMBODIMENTS

This invention describes merocyanine dyes and derivatives that may contain a six-membered aromatic or heteroaromatic ring at the donor end as part of a polyene structure. The six-membered ring renders carbon-carbon double bonds less susceptible to chemical attack, such as oxidation. These merocyanine dyes have been found to possess comparably large (and, in some cases, larger) molecular hyperpolarizabilities when compared to those described in Japanese Patent No. 2,179,624 (Ikeda et al.).

The phenomenon of molecular hyperpolarizability and related NLO effects are described in ACS Symposium Series 233, Am. Chem. Soc'y (Washington D.C. 1983), and in *Angew. Chemie* 96 637–51 (1984). Generally, hyperpolarizable molecules have a delocalized $\pi$-electron system to which both an electron-donor group and an electron-acceptor group are conjugatively coupled directly through the $\pi$-electron system.

Molecules possessing a large molecular hyperpolarizability and a non-zero dipole moment are subject to polar orientation in an electric field. As a result, the composition also becomes macroscopically hyperpolarizable. Such a composition may be used as an optical switch in which the composition is dispersed in a polymer host and an electric field is applied to the hyperpolarizable polymer. Such a use is described by Thackera *Appl. Phys. Lett.* 52 1031 (1988).

The family of merocyanine dyes described by the general formula below is useful in nonlinear optics. These dyes have been found to exhibit exceptionally large molecular hyperpolarizabilities and dipole moments along with very low molar absorbances at 1560 nm, 1300 nm and, in many cases, 830 nm. Low absorbancy at these wavelengths is necessary for use with currently available laser sources, particularly laser diodes.

Merocyanine dyes useful in the present invention are of the general formula:

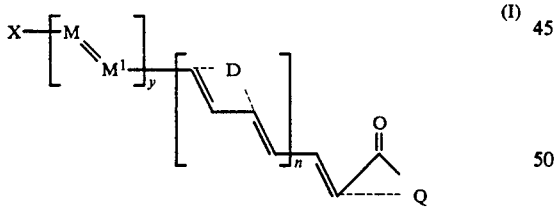

wherein
X is

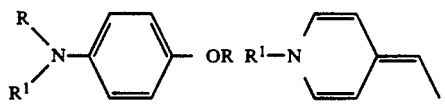

R and $R^1$ are independently an alkyl group or an alkyl group bearing a group bearing an active hydrogen, having 1 to 10 carbon atoms, preferably 1 to 6 carbon atoms, or R and $R^1$ taken together with a nitrogen atom form a heterocyclic nucleus containing five or six atoms in the heterocyclic ring bearing a group bearing an active hydrogen, examples of said nucleus being 2-pyrrolidinomethanol and 4-(2-hydroxyethyl)piperazine;

y is 0 to 2;

M and $M^1$ are independently an olefinic carbon atom or a nitrogen atom, preferably M and $M^1$ are both carbon atoms;

D represents the atoms necessary to complete a cycloalkene ring preferably a 5 or 6 membered ring, wherein the atoms are carbon, and nitrogen, oxygen, or sulfur;

n is 0 or 1; and

Q represents the non-metallic atoms necessary to complete a nucleus of the indandione series, for example 1,3-diketohydrindene, or an unsaturated heterocyclic nucleus containing five or six atoms in its ring, such as those of the isoxazolone series, for example, 3-1'-(2'-hydroxy-2'-phenylethyl)-5-isoxazolone, etc., those of the 2,4,6-triketohexahydropyrimidine series, for example, barbituric acid or 2-thiobarbituric acid) as well as their derivatives containing groups bearing active hydrogens, and/or substituted N-attached phenyl, fluorenyl, or stilbenyl groups where the substituents are electron withdrawing groups such as nitro, trifluoromethyl, or cyano, those of the 2-thio-4-thiazolidinone (rhodanine) series, for example, 3-aminorhodanine, 3-rhodanine acetic acid, and in general a heterocyclic nucleus containing 5 or 6 atoms in the heterocyclic ring and having at least two heteroatoms, such heteroatoms being selected from the group consisting of a nitrogen atom, an oxygen atom, and a sulfur atom, preferably one of the heteroatoms being a nitrogen atom.

A first example of the general formula (I) (y is 0, n is 0, Q is the atoms necessary to complete a 2,4,6-triketohexahydropyrimidine ring) is an N,N,N',N"-tetrasubstituted merocyanine barbituric acid nonlineaphore and is described by the general formula:

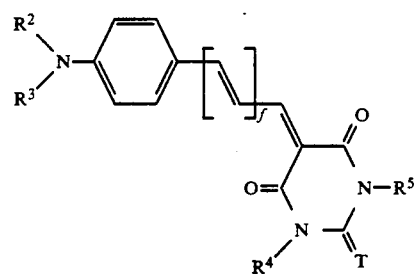

wherein:
T is sulfur or oxygen;
f is 0 or 1;
$R^2$ and $R^3$ are independently an alkyl or an aromatic group or an alkyl or aromatic group bearing a group bearing an active hydrogen, having 1 to 10 carbon atoms, or $R^2$ and $R^3$ taken together to form a heterocyclic nucleus containing 5 or 6 atoms in the heterocyclic ring, which may be substituted with an alkyl group bearing an active hydrogen;
$R^4$ is a substituted phenyl, fluorenyl, or stibenyl group, wherein the substituents are preferably electron withdrawing groups; and
$R^5$ is independently an alkyl or an aromatic group or an alkyl or aromatic group bearing a group bearing an active hydrogen, having 1 to 10 carbon atoms, or $R^4$.

A second example of the general formula (I) (y is 0, n is 0 and Q is the atoms necessary to complete a 2-thio-4-thiazolidinone ring) is an N,N,N'-trisubstituted merocyanine rhodanine nonlineaphore and is described by the general formula:

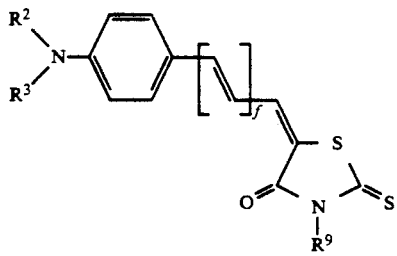

wherein:
f is as defined above;
$R^2$ and $R^3$ are as defined above; and
$R^9$ is independently an alkyl or an aromatic group or an alkyl or aromatic group bearing a group bearing an active hydrogen, having 1 to 10 carbon atoms, or an alkyl group having 1 to 6 carbon atoms, preferably 1 to 2 carbon atoms, bearing an ester group.

A third example of the general formula (I) (y is 0, n is 0 and Q is the atoms necessary to complete a isoxazolone ring) is an N,N,3-isoxazolone-substituted merocyanine isoxazolone nonlineaphore and is described by the general formula:

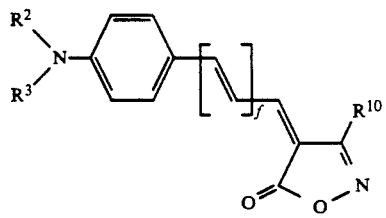

wherein:
f is as defined above;
$R^2$ and $R^3$ are as defined above; and
$R^{10}$ is a substituted alkyl, having 1 to 6 carbon atoms, or a substituted aromatic group having 5 or 6 carbon atoms, wherein the substituents may include halogens, preferably chlorine or fluorine, or a group bearing an active hydrogen.

Compounds of this invention may be prepared as described in U.S. Pat. No. 4,166,740 (Webster et al.) or from the methods described in *J. Amer. Chem. Soc'y* 73 5326 (1951), and such descriptions are incorporated herein by reference.

The present invention provides NLO-active functionalized derivatives and polymers containing such NLO-active functionalized derivatives. The polymers are prepared from functionalized merocyanine dyes that are NLO-active having functionality at both ends of the molecule, such functionality being primary or secondary hydroxy groups, primary or secondary amine groups, esters, or acids. Preferably, the reactivity of the functionality at the donor end is different than the reactivity of the functionality at the acceptor end. Depending on the conditions and the starting materials, functionalized merocyanine dyes can be separated into several subclasses of derivatives. The functionalized derivatives are stable intermediates and may be prepared and stored for a period of time prior to further processing or use in NLO applications.

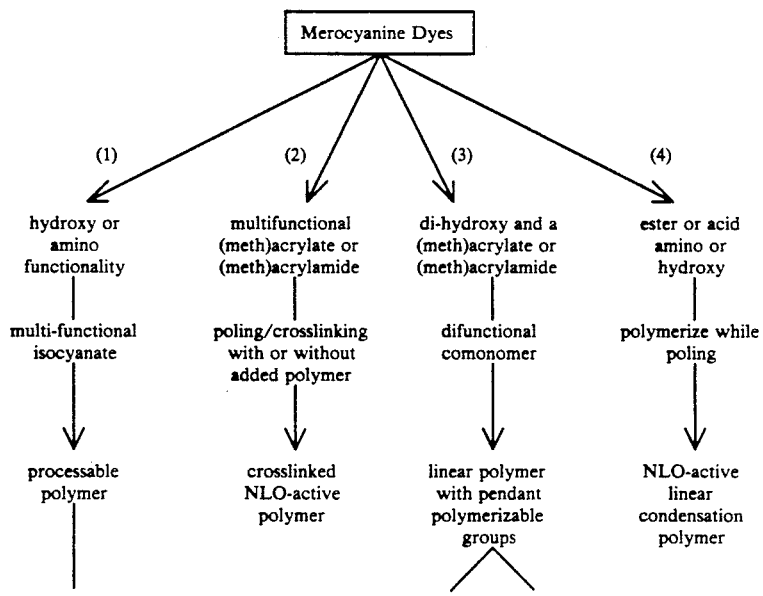

| poling/ | poling/ | -continued<br>use as NLO-active |
|---|---|---|
| crosslinking | crosslinking | viscosifier<br>for Path 2 |
| ↓ | ↓ | ↓ |
| crosslinked<br>NLO-active<br>polymer | crosslinked<br>NLO-active<br>polymer | crosslinked<br>NLO-active<br>polymer |

Functionalized merocyanine dyes are prepared by reacting a functionalized aldehyde with functionalized base acceptor derivatives based on rhodanine, isoxazolone (the "R" group can be any aliphatic or aromatic group), barbituric acid, or thiobarbituric acid structural units as described in the following formulas:

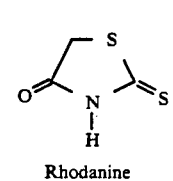

Rhodanine

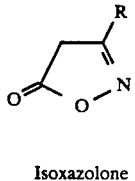

Isoxazolone

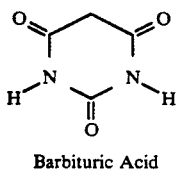

Barbituric Acid

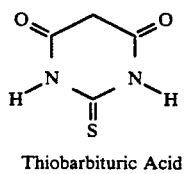

Thiobarbituric Acid

A first subclass, following Path 1, comprises derivatives of merocyanine dyes wherein the derivatives have more than one functionality, that is, a functional group at each end of the molecule, for example, a primary or secondary hydroxyl group, or a primary or secondary amino group. Preferably, the functionalities differ in their reactivities, thus permitting stepwise reaction of each functionality. Advantageously, a soluble polymer or prepolymer is initially synthesized, and can be processed into an optically clear, stable film. This film is then poled and subsequently cross-linked upon heating. The degree of cross-linking is dependent upon, inter alia, the poling temperature and the length of time the film is held at the poling temperature.

A second subclass of the present invention, following Path 2, comprises NLO-active compounds prepared from merocyanine dyes derivatized with (meth)acrylic groups, including acrylic and methacrylic groups, and specifically amides and esters. The functionalized derivatives have (meth)acrylate or (meth)acrylamide functionality at both ends of the compound, that is, a donor end and an acceptor end. Optionally, the NLO-active compounds can be incorporated into linear polymers. The resulting polymer is then used as a polymeric binder or film former. The NLO compounds have a large optical nonlinearity and at least one polymerizable functionality at each end of the extended donor-$\pi$-acceptor system of the functionalized derivative. Attachment of both donor and acceptor ends of the compound within the network (providing cross-linking) severely decreases the mobility of the molecules and leads to increased SHG stability. Polymerization can be thermally or photochemically initiated under poling conditions, depending on the polymerization initiator selected.

A third subclass of the functionalized derivatives of the present invention, following Path 3, comprises derivatives prepared from merocyanine dyes wherein there is functionality at both ends of the donor-$\pi$-acceptor system and preferably the donor end is mono- or difunctional, for example, a primary or secondary hydroxyl group or a primary or secondary amino group, and the acceptor end is a (meth)acrylic or (meth)acrylamide group. Such derivatives can be further processed into linear polymers and can be cross-linked under poling conditions and are NLO-active.

A fourth subclass of the functionalized derivatives of the present invention, following Path 4, comprises derivatives prepared from merocyanine dyes wherein there is a hydroxyl, amino, free or esterified carboxyl group at the one end and a hydroxyl, amino, ester, or acid group at the other end, provided that the groups are reactive towards each other. This subclass of derivatives can be heated to cause condensative melt-polymerization under poling conditions. Although the derivatives are not cross-linked, unlike the members of the other three subclasses, they too are NLO-active.

Most of the functionalized derivatives synthesized thus far have been insufficiently soluble in solvents compatible with the electric field-induced second harmonic technique (EFISH) cell to allow experiments values to be measured. The molecular electro-optic figure of merit (a direct indication of effectiveness in NLO application ) for each isoxazolone-bearing molecule was measured both in 1,2-dichloroethane (DCE), and in poly(methyl methacrylate) (PMMA) by the EFISH. For a full discussion see *J. Chem. Phys.* 66 2664 (1977); and *J. Chem. Phys.* 63 2666 (1975). Similar solubility problems were encountered with the pyridine derivatives. While not being bound by theory, it would appear in theory the pyridine derivatives have efficiencies, defined as $\mu\beta$s, wherein $\mu$ is the dipole moment and $\beta$ is the molecular hyperpolarizbility, of at least twice that of their analogous phenyl derivatives, even though the donor nitrogen atoms and the acceptor group are separated by the same number of conjugating atoms. A description of the theoretical calculations of $\mu$ and $\beta$ values is given in *Proceedings SPIE*, Vol. 1147 48 (1989). These pyridyl derivatives have a significant amount of zwitterionic character and display an unusually high dipole moment.

In addition some of these molecules are difunctional or multifunctional and as such can be used as curing agents for reactive polymers and prepolymers. If they are allowed to react with polymers or prepolymers having reactive ends, they will be incorporated into the polymeric backbone. If the reaction takes place in the presence of the electric field, the nonlineaphores in the backbone will be aligned such that there is an overall polar alignment. Subsequent reorientation of the nonlineaphores is retarded. On the other hand, if the polymer has reactive side chains, the nonlineaphores could react to produce a cross-linked system. Again, if the reaction takes place in the presence of an electric field, the resulting nonlineaphore-containing polymer would have the nonlineaphores aligned more or less parallel such that there is an overall polar alignment. Advantageously, such cross-linked polymers are more resistant to reorientation.

A further advantage of the NLO-active compositions of the present invention is that they may be photobleached at specific wavelengths. Thus, waveguides could be made by selective photobleaching techniques in polymeric films or solids into which these molecules have been incorporated.

Polymers may be derived from the merocyanine dyes through the exploitation of isocyanate chemistry, specifically, by the reaction of amines with isocyanates to produce ureas that can be converted to biurets, and by the reaction of isocyanates with alcohols to form urethanes that can be further converted to allophanates. Urea formation will proceed substantially to completion at room temperature or slightly elevated temperatures, while the urethane/allophanate formation proceeds more slowly under the same conditions, allowing a stepwise reaction and permitting processing of these compositions into cross-linked films.

The NLO molecules are multifunctional, that is they have at least one functional group at each end of the molecule. This is in contrast to the NLO-isocyanate based molecules described in EP 44 5864 A1 (van der Horst) wherein the multifunctionality is confined to one end of the molecule. As a result the remainder of the molecule, in the latter case, has the potential of moving out of alignment to an equilibrium position if the free volume around the molecule is not small enough to severely constrict its motion. This disadvantage is overcome in the present invention by employing donor-π-acceptor molecules having at least one functional group at the donor end of the molecule, and at least one functional group at the acceptor end of the molecule. This enables the molecule to be chemically locked into the orientation as directed by the poling and introduces a large energy barrier (that of bond-breaking) to prevent reorientation of the NLO molecule.

Several polyfunctional isocyanates including the biuret triisocyanate of hexamethylene diisocyanate, the trimer of 2,4-toluenediisocyanate and the oligomer of methylenediphenylisocyanate are commercially available and could be used in this invention. Polyisocyanates based on hexamethylene diisocyanate represent one important class of polyisocyanates. Coatings prepared from these products have excellent resistance to chemicals and abrasion and superior weathering characteristics including resistance to yellowing. Further, films prepared from the isocyanurate triisocyanate are known to exhibit better thermal and weathering properties than films prepared from, for example, the biuret triisocyanate.

The role of the catalyst in isocyanate chemistry is very important. The choice of catalyst will influence the formation of dimers, trimers, allophanates, biurets and other side products. The catalysts most commonly used with isocyanates are tertiary amines and metal catalysts. It is a common practice to use a combination of a tertiary amine and a tin catalyst to exploit synergistic effects as reported by Huynh et al. *Urethane Chemistry and Applications* (Edwards ed., ACS, 1981).

Nonlineaphores derivatized from merocyanine dyes with (meth)acrylates and (meth)acrylamide groups can be described according to the general formula:

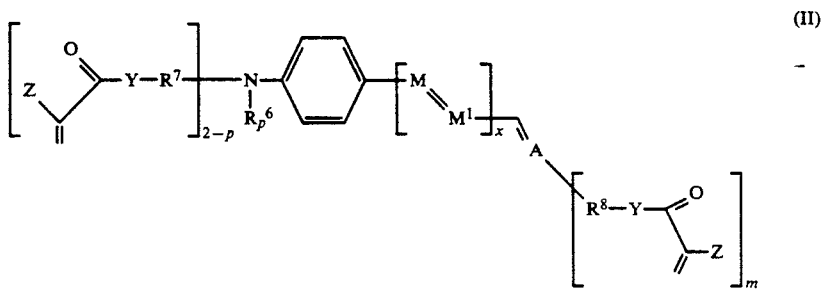

wherein
Z is —CH$_3$ or hydrogen atom;
p is 0 or 1;
Y is oxygen or nitrogen;
R$^6$ is a hydrogen atom or an alkyl group having 1 to 10 carbon atoms, preferably 1 to 6 carbon atoms;
R$^7$ and R$^8$ are independently any connecting group including an alkylene group having 1 to 10 carbon atoms, preferably 2 to 6 carbon atoms;
x is 0 to 2;
m is 0 to 2;
M and M$^1$ are independently an olefinic carbon atom or a nitrogen atoms, preferable M and M$^1$ are both carbon atoms; and
A is any polyvalent electron acceptor group, preferably trivalent, in particular a heterocyclic such as those of the indandione series, for example 1,3-diketohydrindene, or a heterocyclic nucleus containing from five to six atoms in the heterocyclic ring, such as those of the isoxazolone series, for example, 3-phenyl-5(H)-isoxazolone, 3-methyl-5(H)-isoxazolone, those of the 2,4,6-triketohexahydropyrimidine series, for example barbituric acid or 2-thiobarbituric acid, as well as their derivatives containing groups bearing active hydrogen atoms and/or substituted and N-attached phenyl, fluorenyl, or stilbenyl groups where the substituents are electron withdrawing groups such as nitro, trifluoromethyl, or cyano, those of the 2-thio-4-thiazolidinone (rhodanine) series, for example 3-aminorhodanine, 3-rhodanine acetic acid, and in general a heterocyclic nucleus containing 5 or 6 atoms in the heterocyclic ring, and having at least two heteratoms, such heteroatoms being selected from the group consisting of a nitrogen atom, an oxygen atom, or a sulfur atom, preferably one of the heteroatoms being a nitrogen atom.

A first example of the general formula (II) is methacrylated N,N,N',N''-tetrasubstituted merocyanine barbituric acid nonlineaphore and described by the general formula:

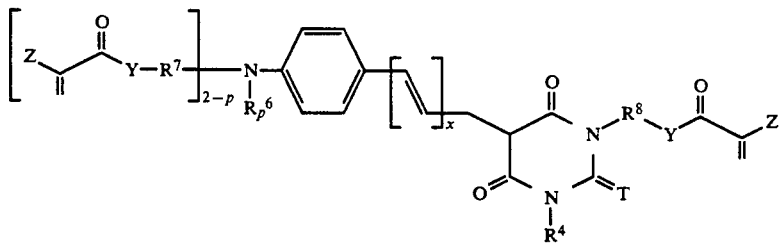

wherein: Y, Z, $R^7$, $R^6$, p, and x are as defined above

A second example of the general formula (II) is methacrylated N,N,N'-trisubstituted merocyanine rhodanine and described by the general formula:

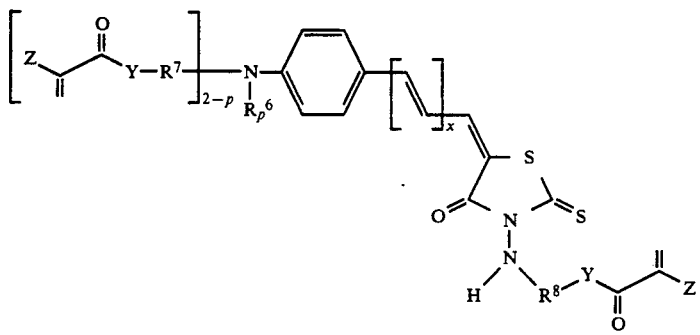

wherein: Y, Z, $R^7$, $R^6$, p, and x are as defined above.

Linear polymers useful in the invention are any polymers that contain the nonlineaphores in the polymer backbone, preferably in the side chain, and more preferably, contain pendant polymerizable groups. Cross-linking of such linear polymers, or of a mixture of such linear polymers and a (meth)acrylated functional nonlineaphore provides a highly crosslinked composition with a high nonlineaphore density.

(Meth)acrylated functional nonlineaphore may be synthesized by reaction of a hydroxyl or amino functionality with isocyanatoethyl (meth)acrylate (IEM), (meth)acryloyl chloride, or (meth)acrylic acid, or by reaction of an acrylic-bearing isocyanate with an acid, such as 3-rhodanine acetic acid.

(Meth)acrylamide functionality has been introduced by reaction of amino or hydroxyl groups with 2-vinyl-substituted azlactones, for example, see Heilmann et al. *J. Polymer Sci. Polym. Chem. Ed.* 22(5) 1179 (1989).

Linear polymers based on the functionalized nonlineaphores may be produced by reaction of bis-hydroxy or hydroxy-amino compounds with difunctional compounds such as diacid chlorides, di-isocyanates, di-acids, or di-esters, or by homopolymerization of the hydroxy-ester compound.

Polymerization of (meth)acrylic functionality using either thermally or photochemically decomposed initiators is well-known in polymer chemistry, see for example, G. Odian *Principles of Polymerization* 194-214 (2d ed. 1981). Incorporation of the nonlineaphore into the polymer network during crosslinking is shown by the failure of the dye to be leached out of the film upon long term exposure to pyridine or methylene chloride, which are good solvents for the dyes.

Clear, glassy films were obtained by spin-coating solutions of (meth)acrylated dyes, or of solutions containing both the nonlineaphores and added polymers. A polymer additive serves to increase the viscosity of the solution, allowing thicker films to be spin-coated, and to increase the viscosity of the melt so that films may be crosslinked at elevated temperatures without flow occurring. The NLO-active, cross-linked polymer system can be derived from a multi-functional (meth)acrylate dye or a mixture of a multifunctional (meth)acrylate dye and a polymer binder that contains the NLO nonlineaphore. By using this polymer as a binder, the solution viscosity is increased without decreasing the nonlineaphore concentration. In all cases a free-radical polymerization initiator was included in the solution.

Poling of the NLO-active molecules of the present invention can be accomplished by any means known in the art. For example, the solution of active molecules may be coated onto a glass substrate between poling electrodes. Preferably, the poling electrodes are vapor deposited onto a glass substrate prior to spin-coating the solution. The dried coating is then heated to a temperature above the glass transition temperature of the coating. An external field in the range of $10^4$ to $10^7$ V·cm$^{-1}$ is applied across the gap (ca. 150 micrometer) between the electrodes, and then the electrodes and coated substrate are cooled to room temperature, whereupon the electric field is removed. The resulting poled polymer will emit a second harmonic frequency when exposed to a laser input. Additional examples of poling are described in U.S. Pat. No. 4,810,338 (DeMartino et al.), and such description is herein incorporated by reference.

A nonlinear-optical component or second harmonic generator of the present invention, such as an optical switch or light modulation device, may comprise the NLO-active composition of the invention as the component itself or as a coating on a substrate. The nonlinear-optical component or device is in the form of a noncentrosymmetric configuration of aligned molecules and the component or device may exhibit a second order effect ($X^{(2)}$) of at least $1 \times 10^{-11}$ esu. A noncentrosymmetric alignment of molecules will have been induced by application of the external field.

A second harmonic generator comprises a laser source of coherent light radiation at a fixed fundamental frequency, an NLO-active composition of the present invention, a means for poling the NLO-active composition, a means for directing the output radiation of the laser onto the poled NLO-active composition to provide output radiation of a second harmonic frequency, and output means for utilizing the resultant second harmonic frequency. Poling means have been discussed hereinabove. A means for directing output radiation of the laser can be a prism or diffraction grating as is known in the art, and an output means can be a prism or diffraction grating, optionally coupled with a filtering device, as is also known in the art.

Additionally, a process for converting a fixed fundamental frequency of coherent laser light into a second-harmonic frequency comprises the steps of: providing an NLO-active composition of the present invention, poling the composition, and passing laser light through the poled polymer to provide output radiation of a second-harmonic frequency, the composition being transparent to the fixed fundamental frequency and to the second-harmonic frequency.

Devices that are capable of generating coherent second-harmonic light radiation are well known in the art. Representative examples of such devices are described in U.S. Pat. Nos. 3,395,329 (Rentzepis et al.), 3,431,484 (Pao et al.), and 3,858,124 (Bass et al.), and such descriptions are incorporated herein by reference for the purpose of describing devices that can incorporate the NLO-active compositions of the present invention, and that also exhibit second-harmonic generation.

Objects and advantages of this invention are further illustrated by the following examples, but the particular materials and amounts thereof recited in these examples, as well as other conditions and details should not be construed to unduly limit this invention.

EXAMPLES

Barbituric acid, thiobarbituric acid, rhodanine, and isoxazolone adducts were all synthesized by similar methods and as such only representative syntheses are shown. Structures were confirmed by at least one spectral analysis selected from UV-VIS (ultraviolet-visible), IR (infrared), $^1$H-NMR (proton nuclear magnetic resonance), and $^{13}$C-NMR (carbon nuclear magnetic resonance) spectroscopies. All starting materials are commercially available or known in the literature, unless otherwise stated or apparent.

EXAMPLE 1

Adduct of 4-Dimethylaminocinnamaldehyde with 3-Phenyl-5-Isoxazolone

This example describes the synthesis of an extended conjugated unfunctionalized isoxazolone dye having both an electron donor group and an electron acceptor group.

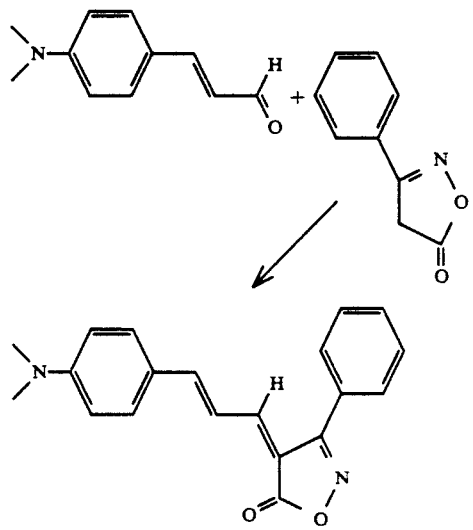

An admixture of 3 grams of 3-phenyl-5-isoxazolone (0.0186 mol) and 3.26 grams of 4-dimethylaminocinnamaldehyde (0.0186 mol) was dissolved in 50 mL of warm toluene. One mL of acetic acid was added and the resulting solution was refluxed for 16 hours. Hot hexane (16 mL) was added to the refluxed solution. From the cooled solution, crystals formed and were filtered off. Recrystallization from toluene:hexane (2:1) produced dark blue crystals, with a melting point (mp) of 162° C. (decomp). In subsequent reactions the reflux time was reduced to 1 hour and the resulting yield was the same. Electro-optic coefficients ($\mu\beta$) measured by EFISH and comparative theoretical values of some isoxazolone adducts are summarized in Table I.

TABLE I

| R | $R^1$ | $R^2$ | EFISH $\mu\beta$ in DCE | EFISH $\mu\beta$ in PMMA | $\mu\beta$ (theoretical) | $\lambda_{max}$ (nm) |
|---|---|---|---|---|---|---|
| —CH$_3$ | —CH$_3$ | —CH$_3$ | 9.8 | 6.92 | 7.5 | 512.5 |
| —CH$_3$ | —CH$_3$ | —CH$_2$CH$_2$CH$_3$ | 6.2 | 7.70 | 7.8 | 515 |
| —CH$_3$ | —CH$_3$ | —C$_6$H$_5$ | 9.5 | 9.18 | 7.8 | 532.5 |
| —CH$_3$ | —CH$_3$ | —CH$_2$Cl | 9.1 | 8.87 | 13.0 | 541 |
| —CH$_3$ | —CH$_3$ | o-FC$_6$H$_4$ | 10.2 | 9.56 | 9.0 | 540 |
| —CH$_3$ | —CH$_3$ | —CF$_3$ | — | 11.6 | 13.9 | 579 |

EXAMPLE 2

Rhodanine Adducts

This example describes the synthesis of amino-functionalized rhodanine adducts. The rhodanine analog can be synthesized by procedures as described in Campbell and McKail *J. Chem. Soc'y* 1251-5 (1948) and by Mackie and Misra *J. Chem. Soc'y* 3919 (1954) and such descriptions are incorporated herein by reference. Alternatively, the rhodanine analog can be synthesized in a manner similar to that used for the isoxazolone adducts.

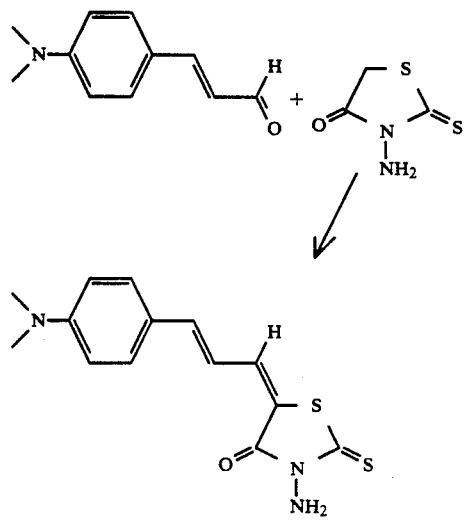

In the case where 3-aminorhodanine had been substituted for the isoxazolone, the measured eletro-optic coefficient figure of merit ($\mu\beta$) was 17 times that of p-nitroaniline, the latter being taken as the standard for $\mu\beta$ ($5.9 \times 10^{-29}$ D esu, $\lambda = 1.9$ micrometers in dioxane). For a discussion of electrooptic coefficients, see Boyd et al. *J. Opt. Soc'y Am.* B(8) 889 (1991). The derivative prepared from rhodanine-3-acetic acid was insoluble in the solvents compatible with the EFISH cell.

EXAMPLE 3

4-[N-ethyl-N-(2'-hydroxyethyl)amino]cinnamaldehyde

This example describes the synthesis of a hydroxy functional cinnamaldehyde as an intermediate to dyes having reactive functionalities. This synthesis is outlined in Scheme 1.

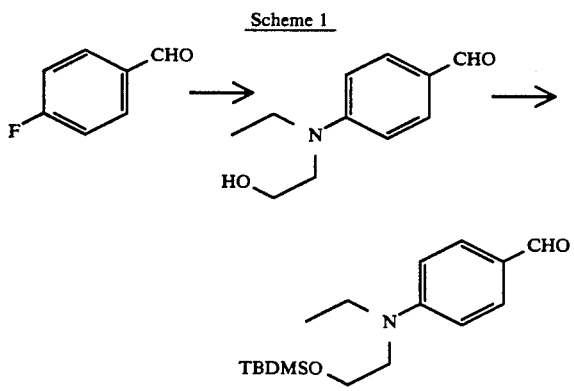

Scheme 1

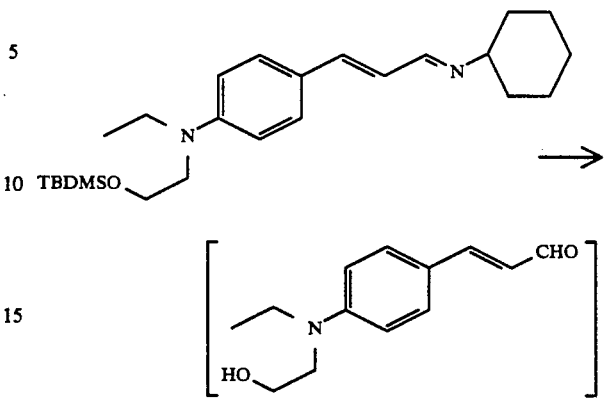

-continued
Scheme 1 a. The general procedure for the preparation of amino subtituted benzaldehyes was adapted from Tournilhac et al. *Liquid Crystals* 2 55 (1987).

4-[N-ethyl-N-(2'-hydroxyethyl)amino]benzaldehyde was prepared by admixing 54.3 grams (0.61 mol) of 2-(ethylamino)ethanol, 50 grams (0.40 mol) of 4-fluorobenzaldehyde, 50 grams of anhydrous potassium carbonate, and 50 mL of dimethyl sulfoxide (DMSO). The solution was heated to 120° C. and maintained at 120° C. for four days under nitrogen atmosphere. Cooled to room temperature, the solution was diluted with one liter of water. The aqueous solution was extracted with dichloromethane and these separated organic layers were combined and processed or worked up in this and appropriate subsequent examples, in a series of steps, called "the organic layer was processed." By this it is meant that the organic layer was separated, dried over anhydrous magnesium sulfate and filtered; and the filtrate was concentrated using a rotary evaporator to provide a residue. The residue was dried at room temperature under vacuum for approximately 18 hours to produce 75.3 grams (96%) of 4-[N-ethyl-N-(2'-hydroxyethyl)amino]benzaldehyde, designated as (A).

b. General procedure for the protection of hydroxalkylamino-substituted benzaldehydes adapted from Corey et al. *J. Am. Chem. Soc'y* 94 6190 (1972). 4-[N-ethyl-N-(2'-t-butyldimethylsiloxyethyl)amino]benzaldehyde was prepared by admixing 100 mL dry dimethyl formamide (DMF), 22.7 grams (0.33 mol) of imidazole and 25 grams (0.16 mol) tert-butyldimethylsilyl (TBDMS) chloride. The resulting solution was heated to 40° C. and maintained under a nitrogen atmosphere for 2.5 hours. 30 grams (0.15 mol) of hydroxyalkylamino benzaldehyde was added to the solution, which was then stirred for an additional 17 hours. The solution was added to 800 mL water and stirred. The aqueous phase was extracted with diethyl ether, the separated organic layer was processed and the residue was dried overnight under vacuum to produce 38.4 grams (80%) of desired product, designated as (B).

c. General procedure for the preparation of protected aminocinnamaldimines:

Three grams (0.1 mol) of an oil dispersion of sodium hydride (80% NaOH) was washed twice with 50 mL dry hexane while under a nitrogen atmosphere. The resulting slurry was dried under vacuum and then combined with 100 mL of dry tetrahydrofuran (THF). The slurry was then cooled in an ice bath and then added dropwise over a period of thirty minutes to a solution of 26 gm (0.1 mol) freshly prepared diethy(phosphonoacetaldehyde cyclohexylimine in 50 mL of dry THF. The reaction mixture was stirred for two hours, and a solution of 30 gm (0.1 mol) or product (B) in 50 mL of dry THF was added dropwise over thirty minutes. After stirring at room temperature overnight, the solvent was removed on a rotary evaporator under reduced pressure at room temperature. The residue was treated with 150 mL water and extracted with diethyl ether. This separated organic layer was processed, and the residue was dried overnight under vacuum to produce 42.4 grams (94%) of aldimine, designated as (C).

d. Procedure for deprotection of aldimine (c) to yield hydroxylalkylamino cinnamaldehyde:

Twenty grams (0.05 mol) of the compound (C) was added to a solution of acetic acid, tetrahydrofuran, and water (3:1:1; total volume was 150 mL) and stirred at room temperature for 48 hours while under a nitrogen atmosphere. The solvent was removed on a rotary evaporator under vacuum to give 23.4 grams of impure composition (D), which was used without further purification.

EXAMPLE 4

Delta-Hydroxy-Beta-ketoester

This example describes the synthesis of a hydroxy functional-ketoester that is an intermediate in the synthesis of a hydroxyfunctional isoxazolone dye.

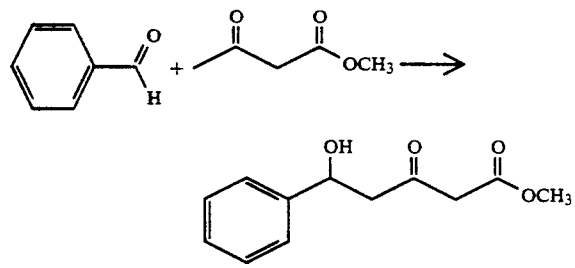

Sodium hydride, as a 80% mineral oil dispersion (3.3 grams, 0.11 mol) was weighed into a 250 mL flask and washed with dry hexane (2×20 mL). Dry THF (50 mL) was then added. The flask was stoppered (septum cap), cooled in ice, and flushed with nitrogen. Methyl acetoacetate (12.74 grams, 0.11 mol) was added dropwise to the cold, stirred slurry. When the addition was complete, the reaction mixture was stirred at 0° C. for an additional 10 minutes. n-Butyllithium (2.5M in THF), (44 mL, 0.11 mol) was then added in a dropwise manner, and the reaction assumed an orange color. The reaction mixture was stirred for 10 minutes before freshly distilled benzaldehyde (11.67 grams, 0.11 mol) was added slowly in a continuous stream. After an additional 10 minutes, the reaction mixture was quenched by the addition of saturated ammonium chloride solution (50 mL) and extracted with ether (4×30 mL). The ether extracts were combined and ether evaporated to give an oily product. 0.6 gram of this oil was purified by flash chromatography using ethyl acetate/hexane (15/85) as eluent to yield the desired product. However, as an improvement, it was found that this particular compound would crystallize if the oil was cooled to −78° C. and ether was added. This latter method yielded 10 grams of product, with a mp of 43°–44° C. This product was used as the delta-hydroxy-beta-ketoester (described in Example 31) in reactions such as the synthesis of the dimethylaminocinnamaldehyde adducts.

EXAMPLE 5

4-(3'-Acetanilidoallylidene)-3-phenyl-5-(4H)-isoxazolone

This example describes the synthesis of an intermediate useful for making dyes with extended conjugation.

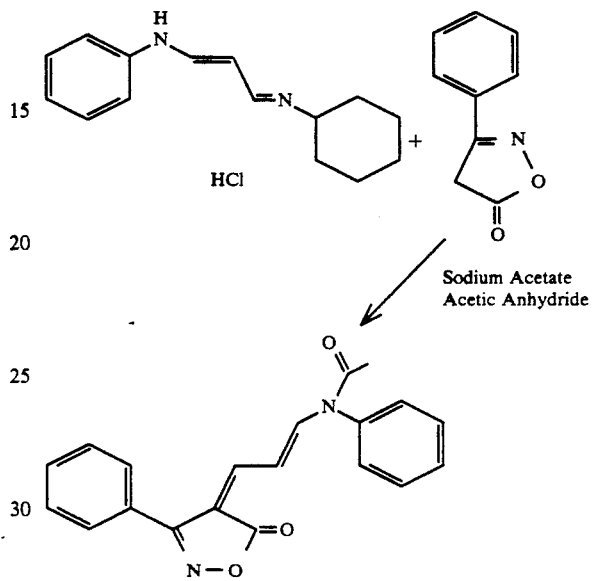

A solution was prepared by admixing 8 grams of 3-phenyl-5-(4H)-isoxazolone (0.05 mol), 12.9 grams of beta-anilinoacrolein anil hydrochloride (0.05 mol), 8.2 grams of sodium acetate (0.1 mol) and 30 mL of acetic anhydride at room temperature. Stirring was continued for about 3 hours until no more product precipitated. The precipitate was filtered off and washed with a large excess of water followed by methanol. Vacuum drying produced 8.6 grams of the desired yellow product.

EXAMPLE 6

N-2'-hydroxyethyl-4-picolinium Iodide

This example describes the synthesis of a hydroxy functional picolinium intermediate useful in the synthesis of hydroxy functional merocyanine dyes.

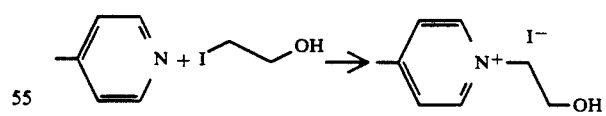

A solution comprising 9.3 grams of picoline (0.1 mol) 17 grams of 2-iodoethanol (0.1 mol), and 50 mL of ethanol was refluxed for 3 hours. The solution was then cooled to room temperature and the solvent removed under vacuum. This resulted in an almost quantitative yield of the desired product.

EXAMPLE 7

Picoline Adduct

This examples describes the synthesis of a hydroxy functional picolinium-isoxazolone adduct.

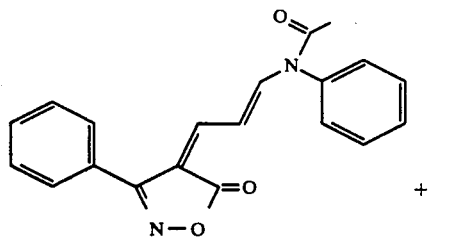

+

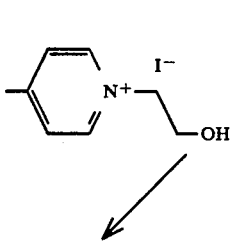

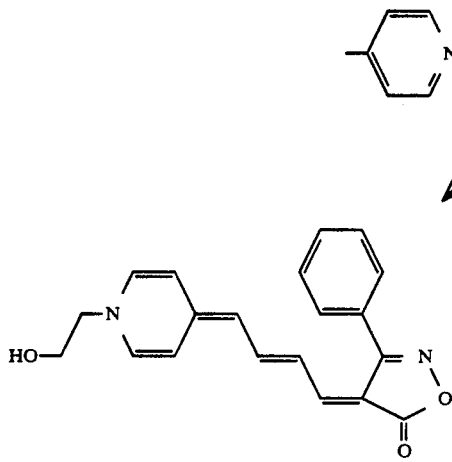

A solution was prepared by admixing 2.7 grams of N-(2-hydroxyethyl)-4-picolinium iodide (0.010 mol), 3.3 grams 4-(3'-(N-acetanilido)allylidene)-3-phenyl-5-(4H) isoxazolone (0.010 mol), 30 mL of ethanol, and 1.7 grams of triethylamine. The solution was refluxed for approximately 2 hours. The mixture was then cooled to room temperature and 30 mL of hexane were added, producing a paste. The hexane layer was decanted and 300 mL of methylene chloride were added to the paste. The mixture was then stirred for about 20 minutes after which 1.7 grams of crystals were collected by filtration. The theoretical $\mu\beta$ of this compound is 24 times that of p-nitroaniline.

EXAMPLE 8

Thiobarbituric cinnamaldehyde adduct

This example describes the synthesis of an unfunctionalized thiobarbituric adduct.

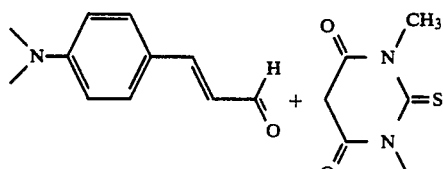

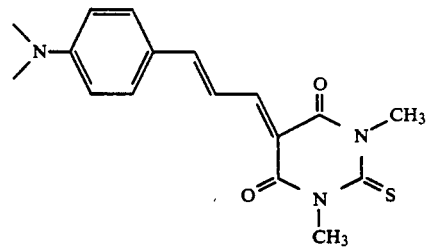

Ten grams of 1,3-dimethyl-2-thiobarbituric acid (0.05 mol) and 2.98 grams of 4-dimethylaminocinnamaldehyde (0.02 mol) were refluxed in warm ethanol (200 mL) to effect solution of the solids. A precipitate formed, and the reaction mixture was refluxed further until no more product was precipitated from the solution. The hot solution was filtered to give an almost quantitative yield of blue solid. The $\mu\beta$ of this compound is 20 times that of p-nitroaniline. The barbituric acid analog that was made in a similar manner had a measured $\mu\beta$ of 12 times that of p-nitroaniline.

EXAMPLE 9

4-[4'-(2''-Hydroxyethyl)piperazino]benzaldehyde

A basic building block for the multifunctional adducts is a hydroxy-functionalized aminobenzaldehyde. This example describes the synthesis of a particular one, but a similar synthesis could be used for other derivatives.

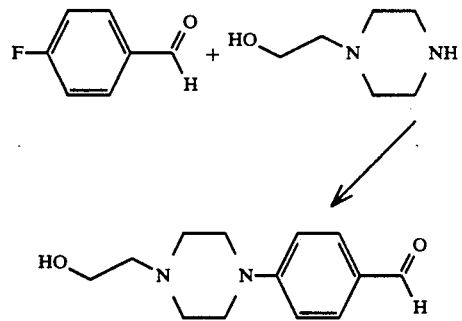

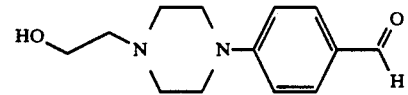

Fifty grams of 4-fluorobenzaldehyde (0.4 mol), 79.0 grams of N-(2'-hydroxyethyl)piperazine (0.4 mol), and 20 grams of potassium carbonate were added to 60 mL of DMSO and stirred at 90° C. for 20 hours. The reaction mixture was then poured into water, stirred and filtered. The resulting solid was washed with ether and then air dried to give 71 grams of product.

EXAMPLE 10

5-[4'-(4''-(2'''-hydroxyethyl)piperazino)benzylidene]thiobarbituric Acid

This example describes the synthesis of a hydroxy trifunctional thiobarbituric acid benzaldehyde adduct.

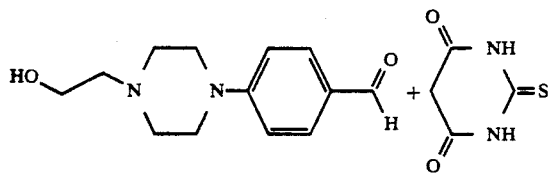

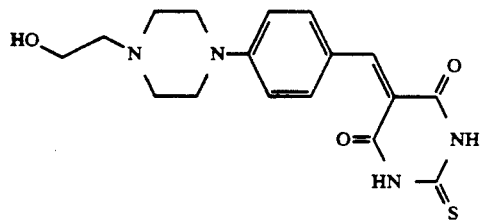

4.68 grams of 4-[4'-(2''-hydroxyethyl)piperazino)]-benzaldehyde (0.02 mol) dissolved in 100 mL ethanol, were added to a 200 mL ethanol solution of 2.88 grams of 4,6-dihydroxy-2-mercaptopyrimidine (0.02 mol). Two mL of diethylamine (0.02 mol) were added, and the resulting solution was refluxed for about 16 hours. The resulting precipitate was collected by filtration, washed several times with hot ethanol, and dried under reduced pressure. The product was obtained as a red solid (73% yield).

EXAMPLE 11

The synthesis of 5-[4'-(4''(2'''-hydroxyethyl) piperazino)benzylidene]barbituric acid proceeded as above with the following exception. After refluxing, the reaction solution was filtered and the filtrate was taken to dryness under reduced pressure. The residue was triturated with ethanol, collected by filtration, and dried under reduced pressure.

EXAMPLE 12

5-[4'-(2''-hydroxyethyl)piperazino]benzylidene-3-aminorhodanine

This example describes the synthesis of a hydroxy bifunctional rhodanine benzaldehyde adduct.

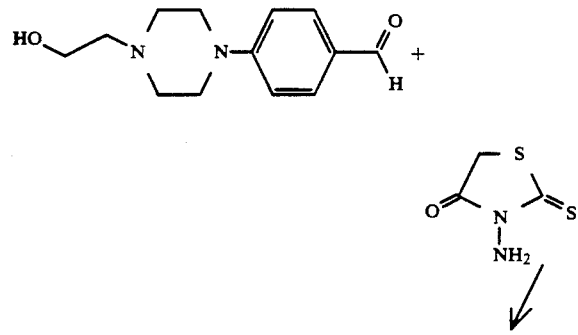

An admixture of 4.7 grams of 4-[4'-(2''-hydroxyethyl)piperazino]benzaldehyde (0.02 mol), 3.0 grams of 3-aminorhodanine (0.02 mol), toluene (30 mL), and glacial acetic acid (5 mL) was refluxed for 4 hours. The admixture was then cooled to room temperature and the solvent was decanted. The remaining paste was triturated with ethanol and then filtered off and dried.

EXAMPLE 13

Synthesis of 4-[4'-(2''-(2'''-hydroxyethyl)ethyl)piperazino]cinnamaldcyclohexylimine (I)

This example describes the synthesis of a hydroxy functional cinnamaldehyde as an intermediate to dyes having reactive functionalities. This synthesis is similar to that outlined in Scheme 2.

a. General procedure for the preparation of hydroxyalkylamino-substituted benzaldehydes adapted from Tournilhac et al. *Liquid Crystals* 2 55 (1987). (See Scheme 1)

4-[4'-(2''-(2'''-hydroxyethoxy)ethyl)piperazino]benzaldehyde (F): A mixture of 54.3 grams (0.61 mol) of N-[2'-(2''-hydroxyethoxy)ethyl]piperazine, 50 grams (0.40 mol) of 4-fluorobenzaldehyde, 50 grams of anhydrous potassium carbonate, and 50 mL of DMSO was heated to 120° C. for four days under nitrogen. After cooling to room temperature, the solution was diluted with one liter of water. The aqueous solution was "processed" as follows. It was extracted with dichloromethane; the separated organic layers were combined and dried over anhydrous magnesium sulfate or sodium sulfate. The organic layer was separated, and solvent was removed on a rotary evaporator under reduced pressure (hereafter these steps will be referred to as "processed" and the product was dried under vacuum overnight to afford 75.3 grams (96%) of 4-[4'-(2''-(2'''-hydroxyethoxy)ethyl)piperazino]benzaldehyde (F).

b. General procedure (see Example 3b, supra for the protection of hydroxyalkyl-aminosubstituted benzaldehydes adapted from Corey et al. *J. Am. Chem. Soc'y* 94 6190 (1972). 4-[4'-(2''-(2'''-t-butyldimethylsiloxy)ethoxy)ethyl-1-piperazino]-benzaldehyde (G): To 100 mL of dry dimethylformamide (DMF) was added 22.7 grams (0.33 mol) of imidazole, and 25 grams (0.16 mol) tert-butyldimethylsilyl (TBDMS) chloride. The mixture was heated to 40° C. and maintained under a nitrogen atmosphere for 2.5 hours. To this mixture was added 30 grams (0.15 mol) of aldehyde (F) and stirred for an additional 17 hours. The reaction mixture was added to 800 mL water and stirred. The aqueous phase was extracted with diethyl ether and "processed" as above. Solvent was removed on a rotary evaporator under reduced pressure and the residue was dried overnight under vacuum to afford 38.4 gm (80%) product (G).

c. General procedure for the preparation of protected piperazinocinnamaldimines,: 3.0 grams (0.1 mol) of an 80% oil dispersion of sodium hydride were washed twice with 50 mL dry hexane under nitrogen atmosphere. The slurry was dried under vacuum and then combined with 100 mL of dry tetrahydrofuran (THF) and cooled on ice. To the slurry was added a solution of 26 grams (0.1 mol) of freshly prepared diethylphosphonoacetaldehyde in 50 mL of dry tetrahydrofuran dropewise over thirty minutes. The reaction was stirred for two hours and a solution of 30 grams (0.1 mol) of product (G) in 50 mL of dry tetrahydrofuran was added dropwise over thirty minutes. After stirring at room temperature overnight, the solvent was removed on a rotary evaporator under reduced pressure at room temperature. The residue was treated with 150 mL of water and extracted with diethyl ether. The organic layer was "processed" as above and solvent was removed on a rotary evaporator under reduced pressure and dried overnight under vacuum to afford 42.4 grams (94%) product H.

d. Alcohol "Deprotection"

The tert-butyldimethylsiloxy protected alcohol of compound (F) (15 grams) was dissolved in a solution of methanol (50 mL) and 1N hydrochloric acid (100 mL). To this was then added concentrated hydrochloric acid (150 mL) and the resulting solution heated on a steam bath for 2 hours. The cooled solution was neutralized with 30% aqueous potassium hydroxide, extracted with chloroform and the chloroform layer washed with water and brine before it was "processed" as above. The chloroform solution on evaporation to dryness under reduced pressure yielded 8 grams of a brown glass, designated as (E).

Compound E and 4-[4'-(2"-hydroxyethyl)piperazino)cinnamaldcyclohexylimine were used as the basic building blocks for the extended conjugated systems.

EXAMPLE 14

5-[4'-(4'-(2'''-hydroxyethyl)]piperazino)cinnamylidene]-thiobarbituric Acid

This example describes the synthesis of a hydroxy trifunctional thiobarbituric acid cinnamaldehyde adduct.

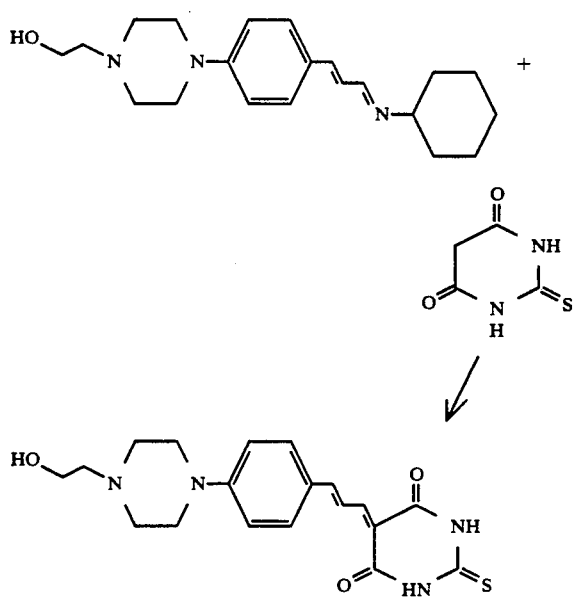

4-[4'-(2"-hydroxyethyl)]piperazino]cinnamaldcyclohexylimine (2 grams., 0.006 mol), dissolved in 100 mL of methanol was added to a 100 mL methanol solution of 4,6-dihydroxy-2-mercaptopyrimidine (0.85 g., 0.006 mol). The resulting solution was refluxed and reaction progress was monitored by thin layer chromotography (TLC). At the end of reaction, the precipitate was collected by filtration, washed several times with hot methanol, and dried under reduced pressure. The product was obtained as a blue solid, (56% yield).

EXAMPLE 15

The 3-aminorhodanine derivative was synthesized similarly to example 14 except that the filtered solution was evaporated to dryness to yield the product.

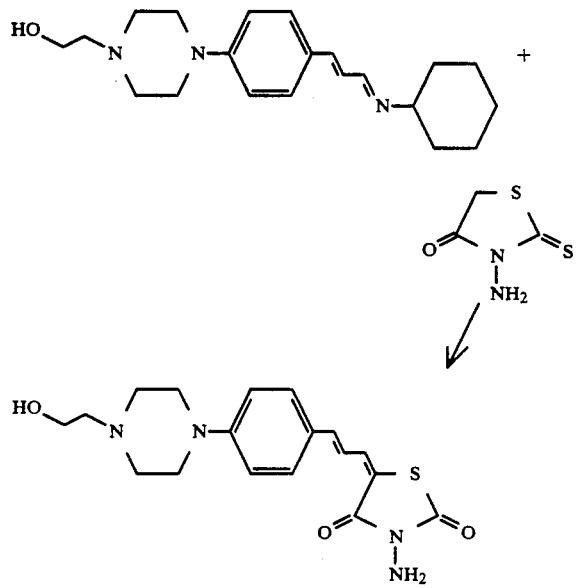

EXAMPLE 16

Polymer Synthesis: Model Reaction

This example illustrates that the amino group of 3-aminorhodanine reacts with a trifunctional isocyanate to give a polymer which can be processed into optical quality films.

The reactionproduct of amino rhodanine and 4-[Bis(2-chloroethyl)amino]benzaldehyde (prepared as described in EPO 0350112, omitting the hydroxy protection step) was synthesized as in Example 12. This product (0.62 gram) was diluted to 5 grams using dry THF and dry DMF (3:2). Tolonate HDT (CAS# 134708-30-8) (Rhone-Poulenc Chem. Co.; 2.7 grams) was made up to 5 grams using dry THF. Equal weights of both solutions were mixed and warmed on a steam bath until a yellow solution was observed. The solution was filtered through a 0.45 micrometer filter in series with a 0.2 micrometer filter before it was spin coated onto a glass slide at 2500 r.p.m. to give a film that was 5 micrometer thick after drying in a vacuum oven at 60° C. for 2 hours.

EXAMPLE 17

Cross-linked Polymer Synthesis (A): Catalytic Solution:

A standard catalytic solution was made and used in examples 17(B) and 18. Dibutylin dilaurate (Alfa Div., Andover, Mass.); 0.3 gram along with triethylene diamine (diazabicyclo[2.2.2.]-octane) (0.2 gram) was made up to 5 grams with dry pyridine.

(B): Polymer from example 12 and Tolonate HDT.

The product from Example 12 (0.18 gram) was diluted to 1.55 grams in a flame dried vial using freshly dried pyridine and warmed on a steam bath to effect solution. Tolonate HDT (0.39 gram) was added and the resultant solution was heated on a steam bath for 1 minute. The solution was filtered through 0.45 micrometer and 0.2 micrometer filters successively, 3 drops of the similarly filtered catalytic solution 17A was added and a film of this mixture was spin-coated onto a glass substrate bearing chromium electrodes having 150 micrometer separation. The film was poled at 150° C. for 16 hours at an applied external field of 1 kV under a continuous flow of nitrogen. The film was cooled to room temperature and the electric field then removed. The film was subsequently heated to 100° C., with no electric field applied, and held there for 6 days while monitoring the second harmonic generation (SHG) response. No decrease in the SHG signal was observed. The film was then heated to 175° C. whereupon the SHG signal intensity decreased to 15% of its initial value. At this point the electric field was again applied and the SHG signal was restored to its initial stable value.

EXAMPLE 18

Polymer from Example 11 and Tolonate HDT.

Tolonate HDT (2.77 grams) and the product from Example 11 (0.21 gram) were allowed to react as in example 17B. A film was spin-coated onto a glass substrate bearing chromium electrodes at 150 micrometer separation and poled at 102° C. for 70 minutes. No change in the SHG signal was observed when the electric field was removed at room temperature. Raising the temperature of the poled film showed no signs of SHG signal decrease below 90° C.

EXAMPLE 19

This examples describes the synthesis of a bis-methacrylated rhodanine dye.

(A) N-(3-rhodanino)-N'-(2''-methacryloyloxyethyl)urea

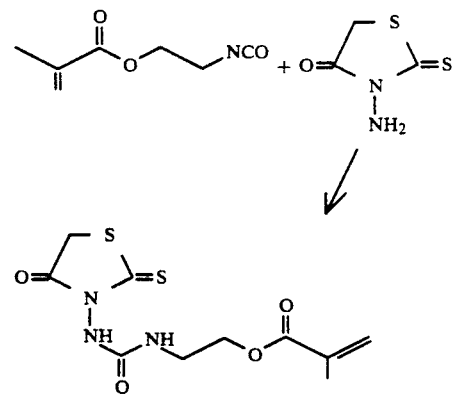

3-aminorhodanine (Aldrich Chemical Co., 1.5 grams, 0.010 mol), 15 drops of dibutyltin dilaurate and 0.05 grams triethylenediamine were added to 50 milliliters (mL) dry pyridine. Isocyanatoethyl methacrylate (Dow Chemical Co., 1.5 mL, 0.010 mol) was then added and the solution was stirred at room temperature for approximately 30 minutes. After this time, 20 mL of ethanol was added, and the solvents were removed be means of a rotary evaporator. The residual tan solid (80% yield) was collected, and rinsed with ethanol.

(B) 4-(4'-(2''-methacryloyloxyethyl)piperazino]benzaldehyde

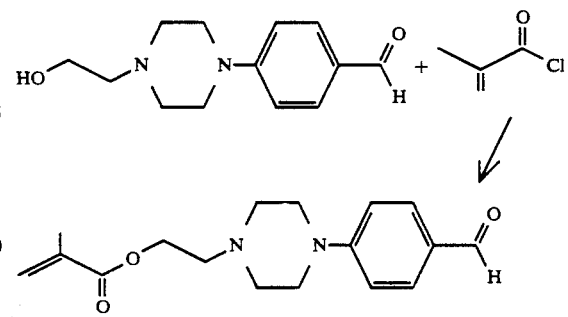

4-[4'-(2''-hydroxyethyl)piperazino]benzaldehyde was prepared as described in Tournilhac et al. *Liquid Crystal* 2 55 (1987). 4-[4'-(2''-hydroxyethyl)piperazino]benzaldehyde (7.4 grams, 0.031 mol) was dissolved in 50 mL $CH_2Cl_2$ and 10 mL triethylamine. The solution was stirred at room temperature and 3.04 mL (3.2 grams, 0.031 mol) methacryloyl chloride was added. After approximately 30 minutes, the insoluble amine salt was removed by filtration, and the $CH_2Cl_2$ solution was rinsed three times with 0.1M $NaHCO_3$ solution. The solution was dried over $MgSO_4$, filtered, and the filtrate was concentrated to yield 9 grams (94% yield) of a yellow solid.

(C) Piperazino-rhodanine dimethacrylate dye

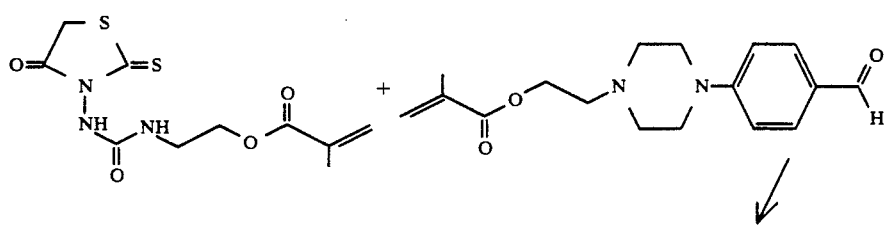

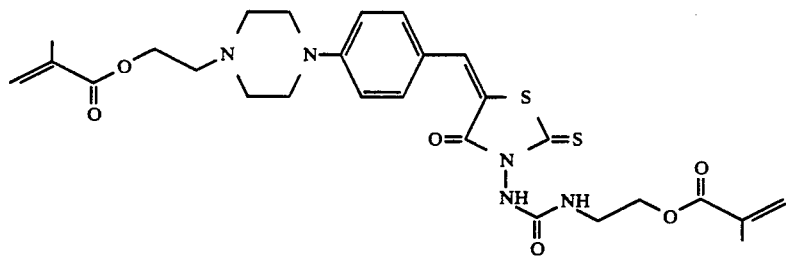

N-(3-rhodanino)-N'-(2"-methacryloyloxyethyl)urea (1.6 grams, 0.0053 mol) and 4-[4'-(2"-methacryloyloxyethyl)piperazino)]benzaldehyde (1.6 grams, 0.0053 mol) were added to a round-bottomed flask containing 300 mL of ethanol. The solution was refluxed for 1 hour at which time the solution was filtered hot and then cooled. The resulting red precipitate (2.2 grams, 66% yield) was collected and rinsed with cold isopropanol.

EXAMPLE 20

The example describes the synthesis of a tris-methacryloyl rhodanine nonlineaphore.

(A) 3-amino-5-[4'-(N,N-bis-(2"-hydroxyethyl)amino)-benzylidene]rhodanine

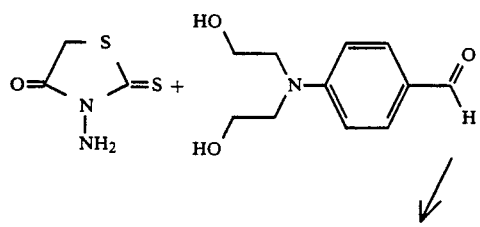

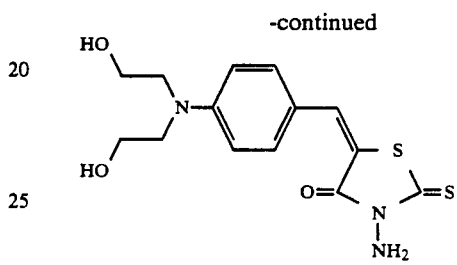

3-Aminorhodanine and 4-[N,N-bis-(2'-hydroxyethyl)amino]benzaldehyde, prepared according to the method described in EPA 0 350 112, were condensed as described in Example 19 (C) by refluxing in ethanol. On cooling to room temperature the product precipitated out of solution. The precipitate was filtered and air dried.

(B) Tris-methacryloyl rhodanine nonlineaphore

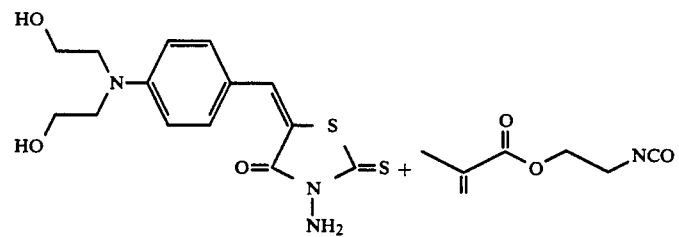

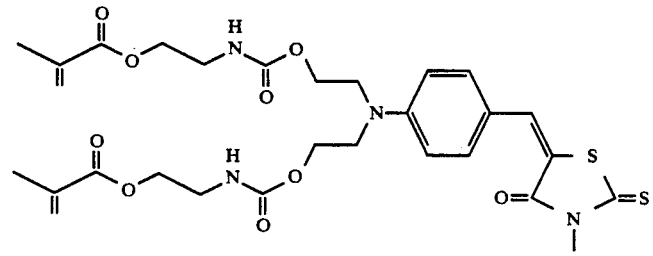

3-amino-5-[4'-(N,N-bis-(2''-hydroxyethyl)amino)benzylidene]rhodanine (1 gram, 0.003 mol) was dissolved in 20 mL dry pyridine along with 0.1 gram triethylene diamine and 5 drops dibutyltin dilaurate as catalysts. 2-Isocyanatoethylmethacrylate (1.5 mL, 0.009 mol) was then added. The solution was heated to reflux for 10 minutes, at which time 10 mL of ethanol was added and the solvent was evaporated. A red oily product was obtained and triturated in ethanol. A red-orange precipitate was later collected.

EXAMPLE 21

This example describes the synthesis of a methacrylated barbituric acid nonlineaphore.

1-phenyl-3-(2'-hydroxyethyl)barbituric acid was synthesized according to the method described in *Organic Synthesis* Vol. 2, p 60 (A. H. Blatt ed. 1943).

(A) 1-phenyl-3-(2'-hydroxyethyl)-5-[4''-N-ethyl-N-(2'''hydroxyethylamino)benzylidene]barbituric acid

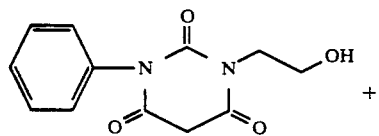

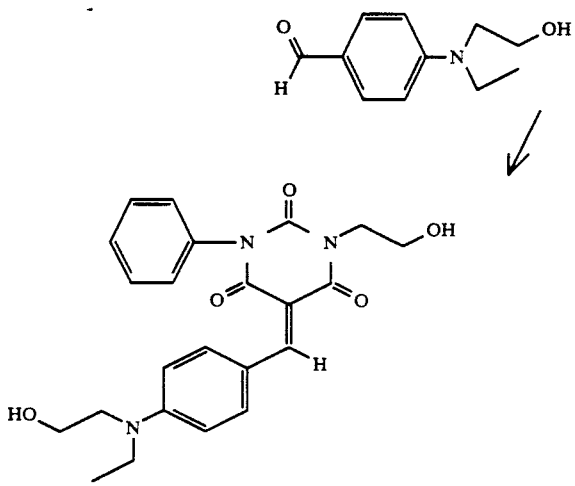

1-phenyl-3-(2'-hydroxyethyl)barbituric acid was condensed with 4-[N-ethyl-N-(2'-hydroxyethyl)amino]benzaldehyde in ethanol according the procedure of Example 19 (C). The product was a mixture of Z and E isomers.

(B) Preparation of bis-methacrylated barbituric acid nonlineaphores

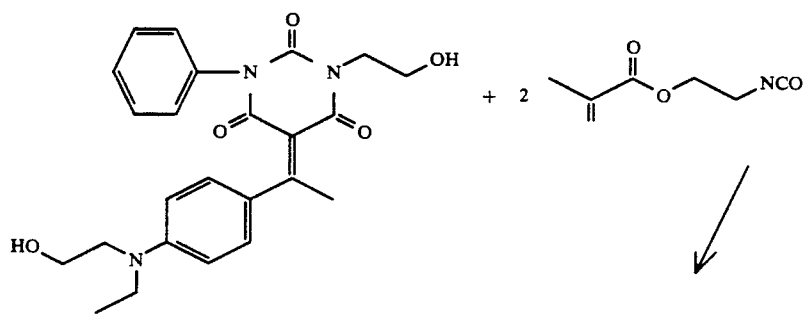

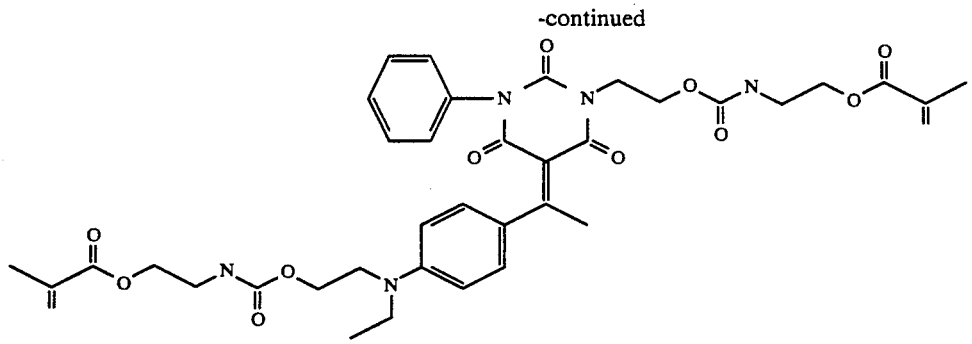

Bis-hydroxyethylated dye (0.5 gram, 0.0012 mol) was dissolved in 20 mL dry pyridine along with 0.1 gram triethylene diamine and 5 drops dibutyltin dilaurate as catalysts. Isocyanatoethyl methacrylate (0.4 mL, 0.0024 mol) was then added. The solution was heated to reflux for 10 minutes, at which time 10 mL of ethanol was added, and the solution was concentrated by evaporation. A red oily product was obtained, that was then dissolved in ethanol. A red-orange precipitate was later collected.

EXAMPLE 22

This example describes the synthesis of a methacrylate-functionalized polymer containing a dihydroxy-functional rhodanine-benzylidene nonlineaphore.

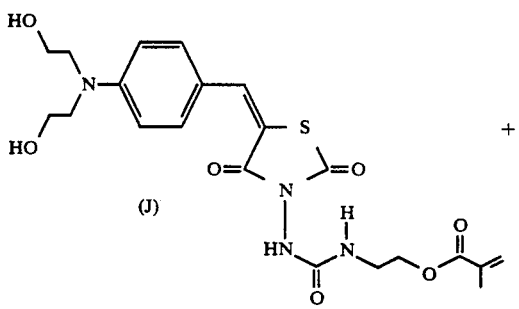

(J)

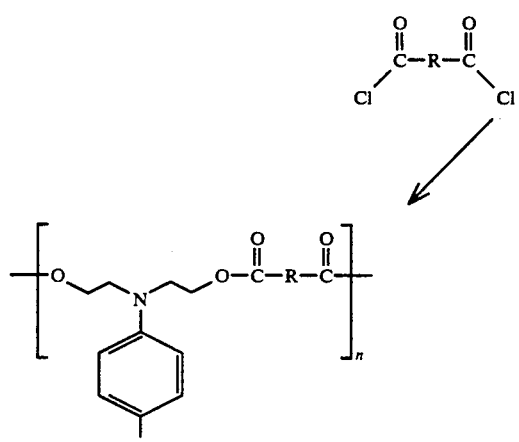

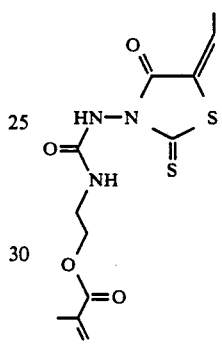

Compound J was synthesized by condensation of 4-[bis-(2'-hydroxyethyl)amino]benzaldehyde, prepared according to the method described in EPA 0 350 112, with N-(3-rhodanino)-N'-(2''-methacryloyloxyethyl-)urea, prepared according to the method described in Example 18 (A).

Compound J (1.0 gram, 0.002 mol) was dissolved in 100 mL of dry pyridine. Phthaloyl chloride (0.41 gram, 2 mmoles) was then added dropwise. The solution was stirred at room temperature overnight, under nitrogen. The polymer was then precipitated by pouring the solution into cold methanol.

EXAMPLE 23

This example describes the poling and crosslinking of films containing a multifunctional methacrylate nonlineaphore.

A solution was prepared containing, 0.170 gram bis-methacryloyl rhodanine dye (Example 19), 0.011 gram 2,2-dimethoxy-2-phenyl-acetophenone (initiator), and 1.0 gram tetrahydrofuran.

The solution was spin-coated on a glass slide having two coplanar chromium electrodes, spaced 150 micrometers apart. After removal of the solvent in a vacuum oven, the composition was poled at $6.7 \times 10^4$ $V \cdot cm^{-1}$ external field and irradiated by an Ultraviolet Products Mineralite TM lamp (0.33 $mW \cdot cm^{-2}$, 350 nm) for 1.5 hours at a temperature of 160° C. Upon cooling to 100° C. and removal of the electric field, the SHG signal fell to about ½ of its initial value but the residual signal was stable at 100° C. for up to eight weeks.

A complete description of the polymer poling process is described in Boyd et al. *J. Opt. Soc'y Am.B.* 8(4) 889 (1991).

EXAMPLE 24

This example describes the poling and crosslinking of films containing a multifunctional methacrylate nonlineaphore and a polymer binder.

A solution was prepared containing 0.98 gram of bis-methacryloyl rhodanine dye (Example 19), 0.32 gram of poly(2-hydroxyethylmethacrylate), 8 mL of pyridine, and 0.66 gram of 2,2-dimethoxy-2-phenylacetophenone.

The solution was spin coated onto a glass slide having two coplanar chromium electrodes. After removal of the solvent in a vacuum oven, the composition was poled with $6.7 \times 10^4$ V·cm$^{-1}$ external field and irradiated by an Ultraviolet Products Mineralite ™ lamp (0.33 mW·cm$^{-2}$, 350 nm) for 2 hours at a temperature of 160° C. The composition was cooled to 100° C., the electric field removed and the SHG signal monitored. Over a period of several days, the SHG signal fell to approximately 80% of the initial value after the electric field was removed. The SHG signal then remained stable for at least 15 weeks.

A similar solution using the polymer synthesized in Example 22 in place of the above poly[(2-hydroxyethyl)methacrylate] was made, formed optically clear films, and crosslinked under poling conditions as described above.

EXAMPLE 25

3-(2''-hydroxyethyl)-1-(4'-nitrophenyl)-5-[4''''-(N-ethyl-N-(2''''-hydroxyethyl)amino)benzylidene]barbituric acid This example describes the synthesis of a difunctional nitrophenyl barbituric acid dye starting from the corresponding nitrophenyl isocyanate.

(A) N-(2-hydroxyethyl)-N'-(4-nitrophenyl)urea

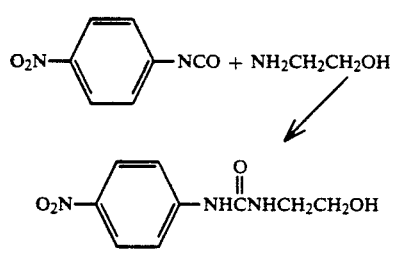

4-Nitrophenyl isocyanate (45 grams, 0.27 mol) was added dropwise to a solution of ethanolamine (16.7 grams, 0.27 mol) in THF (200 mL) with stirring. After the addition was complete, stirring was continued for three hours. The precipitate was filtered off and washed repeatedly with THF. N-(2-hydroxypropyl)-N'-(4-nitrophenyl) urea was prepared similarly using amino-2-propanol. This product was used in cases where a secondary alcohol was required at the acceptor end of the dye.

(B) 3-(2''-hydroxyethyl)-1-(4'-nitrophenyl)barbituric acid

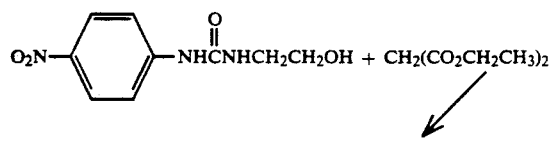

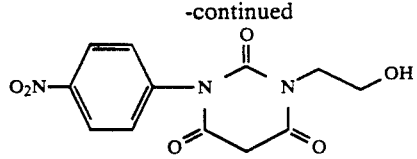

In a 1 liter round-bottom flask equipped with an overhead stirrer and reflux condenser was placed N-(2-hydroxyethyl)-N'-(4-nitrophenyl)urea (40.0 grams, 0.178 mol), diethyl malonate (71.2 grams, 0.445 mol), and ethanol (560 mL). Sodium ethoxide in ethanol (21 wt %, 69.2 grams, 0.214 mol) was added and the reaction mixture was heated to reflux for 6 hours. The reaction mixture was cooled and the ethanol was removed under vacuum. Methylene chloride (500 mL) and water (500 mL) were added. The layers were separated and the aqueous layer was further washed with a second portion of methylene chloride to extract a by-product, 4-nitroaniline which was discarded. The aqueous layer was acidified with 6N HCl (50 mL) and an oily phase precipitated. The oil layer was separated and stirred with 70 mL of benzene. After several minutes the oil turned into a chunky, aggregated solid. The benzene was decanted off and the chunky solid was broken up and triturated with hot benzene. The solution was cooled and suction filtered to isolate the solid, which was oven-dried yielding N-(2-hydroxyethyl)barbituric acid (29.4 grams). Additional product (6.2 grams) crystallized out of the water layer upon standing overnight. The additional product was collected by suction filtration and dried.

(C) 1-(4-Nitrophenyl)-3-(2''-hydroxyethyl)-5-[4''''-N-ethyl-N-2''''-hydroxyethyl)aminobenzylidene]barbituric acid.

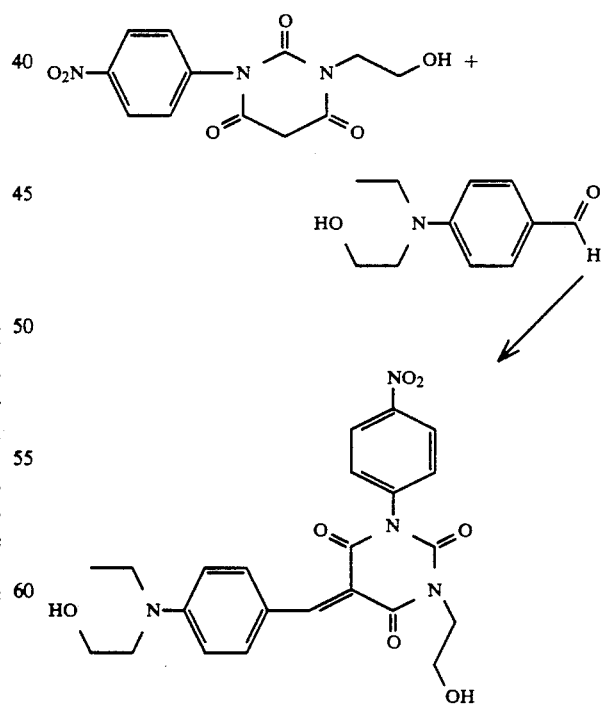

A solution of 3-(2''-hydroxyethyl)-1-(4'-nitrophenyl)-barbituric acid (4 grams, 0.015 mol) in ethanol (100 mL) is added to a solution of 4''''-N-ethyl-N-(2''''-hydroxyethyl)aminobenzaldehyde (2.9 grams, 0.015 mol) in ethanol (100 mL). The resulting solution was refluxed for approximately 20 hours. The orange precipitate was filtered off and washed repeatedly with ethanol, then dried.

1-(4'-Nitrophenyl)-3-(2''-aminoethyl)-5-[4'''-(N-ethyl-N-2''''-hydroxyethyl)amino)benzylidene]barbituric acid; 1-(4'-nitrophenyl)-3-(2''-hydroxypropyl)-5-[4'''-(N-ethyl-N-(2''''-hydroxyethyl)amino)benzylidene]barbituric acid; and 1-(4'-nitrophenyl)-3-(2''-hydroxyethyl)-5-[4'''-(N-ethyl-N-(2''''-hydroxypropyl)amino)-benzylidene]barbituric acid can also be prepared according to the procedure outlined above. Also other phenyl-substituted derivatives such as cyanophenyl and trifluoromethylphenyl can be synthesized in a similar manner, starting from the corresponding isocyanate.

EXAMPLE 26

This example illustrates that the hydroxy and/or amino group of the barbituric acid adduct of Example 25 can react with a trifunctional isocyanate to produce a polymer that can be processed into optical quality films.

1-(4-Nitrophenyl)-3-(2''-hydroxyethyl)-5-[4'''-N-ethyl-N-(2''''-hydroxypropyl)amino)benzylidene]barbituric acid (0.574 gram) was dissolved in 2 mL of pyridine with slight heating. This solution was poured into Tolonate HDT (1.1 eq.). The resulting solution was shaken at room temperature for 2 minutes and subsequently heated at 50° C. for thirty minutes. The solution was spin-coated onto chromium electrodes to make optical quality films which were poled as in Example 17B.

EXAMPLE 27

1-[(7'-Nitro-2'-fluorenyl)-3-(2''-hydroxyethyl)]urea

This example describes the synthesis of a urea nonlineaphore intermediate starting from a dinitro compound. From the latter the amino-nitro compound is synthesized and then converted to the nitroisocyanate compound. At this point one could also react the aminonitro compound with the appropriate isocyanate to produce the desired urea.

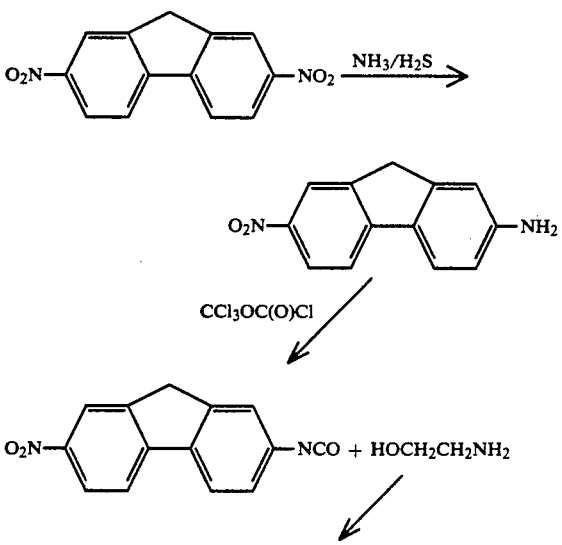

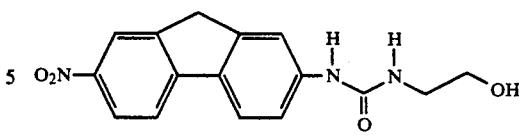

2,7-Dinitrofluorene (TCI Chem. Co., 10.0 grams) was added to a solution of ethanol (600 mL) and concentrated ammonia (70 mL) and warmed to 65° C. before a steady stream of hydrogen sulfide is bubbled through the mixture. After about 3 hours, the reaction was stopped and the mixture allowed to cool to room temperature. The red crystals were isolated by filteration and washed with copious amounts of water and then with cold ethanol (200 mL). In some cases the product was also washed with carbon disulfide and air dried. Yields were on the order of 75-80% pure 2-amino-7-nitrofluorene.

In a flask fitted with an air-cooled condenser was added 2-amino-7-nitrofluorene (2.26 grams), ethylene dichloride (25.0 grams) and trichloromethylchloroformate (1.98 grams). The reaction mixture was heated on a steam bath for about 16 hours before the hot mixture was filtered and the solids washed with ethylene dichloride (25 grams). To the combined filtrate was added hot isooctane (50 grams) and the resulting solution allowed to cool to room temperature. The crystals were filtered off, washed with isooctane, and dried at 100° C. to produce 0.98 gram of a yellow solid, m.p. 198°-200° C. A second crop of solid was obtained by evaporation of the filtrate down to 20 mL and the addition of isooctane (100 mL). This solid was digested at 80° C. for 1 hour before it was filtered off and washed with additional isooctane to give 1.38 grams, m.p. 188°-192° C. A total yield of 2.36 grams (93%) was obtained. This product, 7-nitro-2-fluorenylisocyanate, contained some yellow infusible solids, but was still useable. In similar fashion was made 4'-nitrostilbene-4-isocyanate, having m.p. 170° C. (98% yield). These nonlineaphores are preferred on the basis of theoretical calculations, $\mu\beta$ being larger for these than for 4'-nitrobiphenyl-4-isocyanate. The corresponding nitroisocyanates of biphenyl, phenanthrene, dihydrophenanthrene, and naphthalene are synthesized similarly.

7-Nitro-2-fluorenylisocyanate (4.2 grams, 0.017 mol) was added dropwise to a solution of ethanolamine (1 gram, 0.017 mol) in THF (100 mL) with stirring. After the addition was complete, stirring was continued for three hours. The precipitate of 1-(7'-nitro-2'-fluorenyl)-3-(2''-hydroxyethyl)urea was filtered off and washed repeatedly with THF to produce 1-(2''-nitrofluorenyl)-3-(2'-hydroxyethyl)urea. This may be used as in example 26B to make functionalized barbituric acid. In similar fashion is made 1-(4'-nitro-4-stilbenyl)-3-(2''-hydroxyethyl)urea, useful in the same way. These nonlineaphores are preferred for the aforesaid reason, however any 1-(polynuclear-nitroaryl)-3-(2'-hydroxyethyl)urea may be used for this purpose.

EXAMPLE 28

Synthesis of poly{3-methylaceto-5-[4'-(N-(2''-hydroxyethyl)-N-ethyl)amino)benzylidene]rhodanine}

(A) Synthesis of rhodanine methylacetate

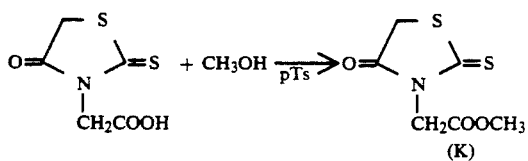

Rhodanine acetic acid (Aldrich Chem. Co. 4.0 grams) was refluxed in methanol (30 mL) with p-toluene sulfonic acid (pTs) (0.01 gram) for 3 hours after which the excess methanol was removed with a rotary evaporator. The residue was washed with saturated sodium bicarbonate and then extracted with four 30 mL portions of methylene chloride. The combined extracts were dried over anhydrous magnesium sulfate and the solvent evaporated to give a viscous yellow residue.

(B) Synthesis of the benzaldehyde condensation product

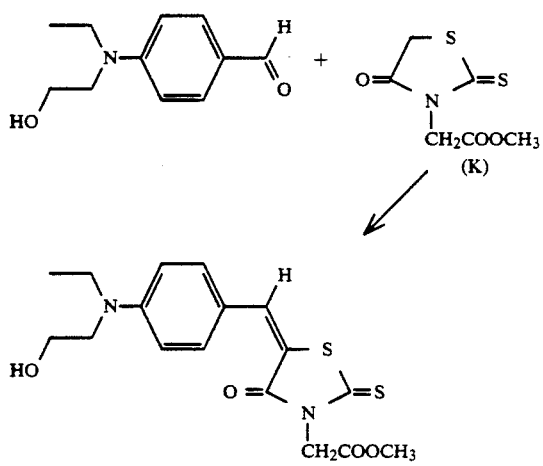

Methyl rhodanine-N-acetate, (K) (2.3 grams) was dissolved in methanol (15 mL) along with 4-(N-ethyl-N-(2'-hydroxyethyl)aminobenzaldehyde (2.2 grams) and allowed to sit at room temperature until no more product precipitated. In subsequent reactions this solution was refluxed for 1 hours, allowed to cool to room temperature and the product was filtered.

(C) Polymer synthesis

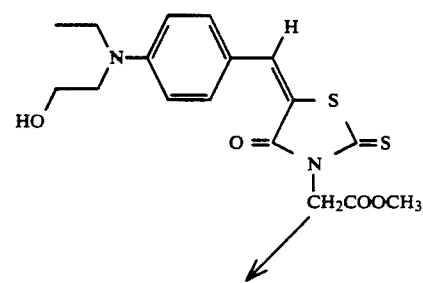

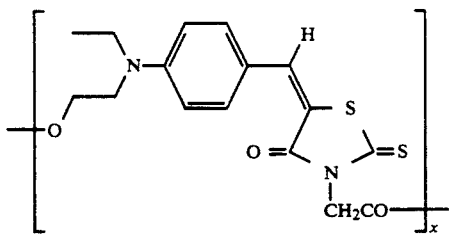

The hydroxy acetate synthesized in Example 28(B) (0.5 gram) was heated under nitrogen at 150° C. for approximately 7 hours. The product had a number average molecular weight in the range of 6,000–7,000 with a polydispersity of 1.4, as determined by GPC, using polystyrene as a standard.

This polymer was spin-coated onto chromium electrodes, poled and further polymerized during poling.

EXAMPLE 29

N-Ethyl-N-(2-hydroxypropyl)amine

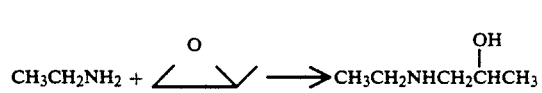

In a 500 mL 3-necked round-bottomed flask equipped with a dry ice condenser was placed 100 grams of ethylamine. Tetrabutylammonium chloride hydrate (8.0 grams) was dissolved in 50 mL ethanol and added to 59.0 grams of propylene oxide. This solution was slowly added to the flask containing the amine. After complete addition, the reaction mixture was refluxed at 35° C. for approximately 8 hours. The temperature was then increased to 90°–95° C. and the reaction mixture was refluxed for approximately 4 hours. The product (a colorless liquid) was isolated by atmospheric-pressure distillation (155° C.).

EXAMPLE 30

4-[N-ethyl)-N-(2'-hydroxypropyl)amino]benzaldehyde

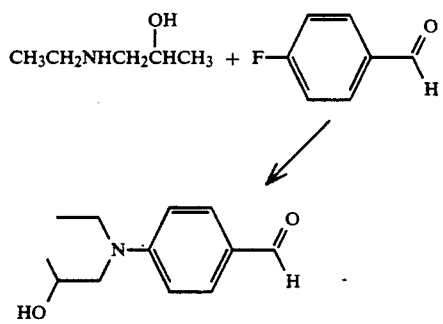

This compound was synthesized according to the procedure of Example 3(A). The product was purified using column chromotography with a silica support and methylene chloride/acetone (85/15) as the eluent and on evaporation of the solvent, the desired product was obtained. The aldehyde was used to make dyes containing a secondary hydroxy group at the donor end of the molecule.

EXAMPLE 31

This example described the synthesis of a hydroxy-functionalized isoxazolone nonlineaphore.

To a solution of a delta-hydroxy-beta-ketoester (prepared according to Example 4) (2.22 grams) in ethanol (20 mL) was added as an aqueous solution of hydroxyl amine hydrochloride (0.695 gram) and sodium acetate (1.06 grams) in water (12 mL). The mixture was heated under reflux for about 2 hours and then allowed to cool to room temperature. The reaction mixture was then extracted with ethyl acetate, dried over anhydrous magnesium sulfate and the dried extract evaporated to give 1.65 grams of the hydroxy-functionalized isoxazolone.

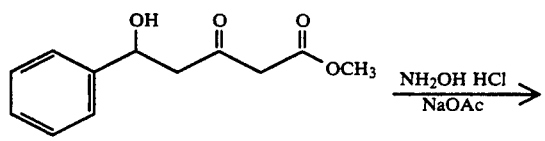

4-(N,N-dimethylamino)cinnamaldehyde (1.4 grams) was added to the hydroxy-functionalized isoxazolone (1.6 grams) dissolved in ethanol and refluxed for about 0.5 hour. The solution was cooled in an ice bath and filtered. The filtrate was further cooled and filtered to produce 0.8 gram of the hydroxy-functionalized merocyanine dye.

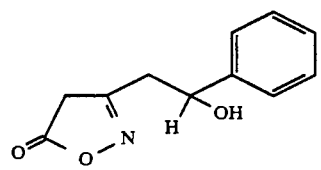

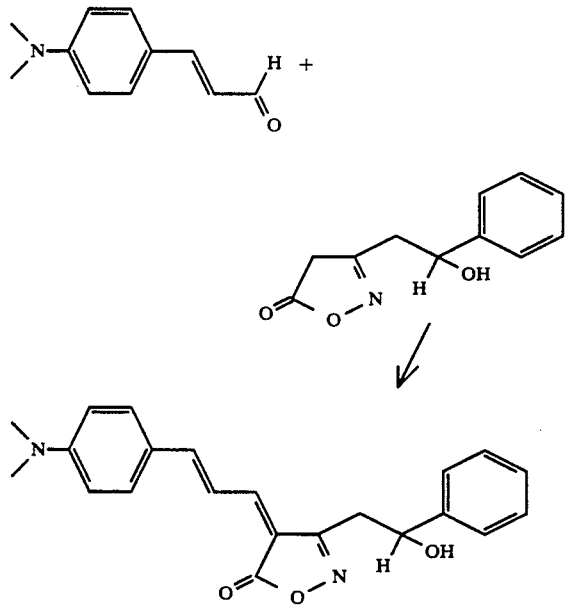

EXAMPLE 32

This example describes the synthesis of a difunctionalized diazo-nonlineaphore.

(A) Synthesis of naphthalic anhydride dye

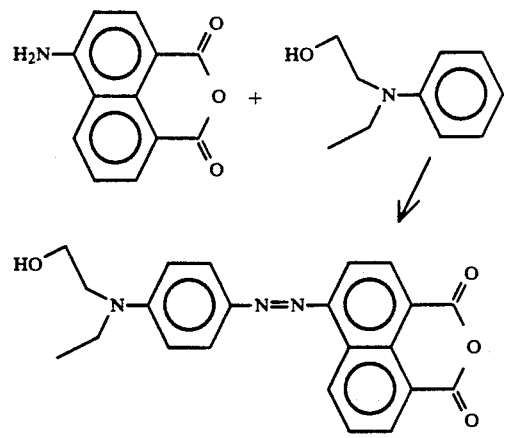

Sodium nitrate (1.6 grams, 0.023 mol) was added to 20 mL cold (<10° C.) concentrated $H_2SO_4$. 4-Amino-1,8-naphthalic anhydride (5 grams, 0.023 mol) was added slowly with stirring, keeping the temperature less than 10° C. The diazotization was continued for two hours.

N-Ethyl-N-phenylethanolamine (3.8 grams, 0.023 mol) was dissolved in 20 mL concentrated HCl and cooled to less than 10° C. The diazo solution was slowly added to the HCl solution with stirring, keeping the temperature less than 10° C. The solution was stirred for two hours, then poured into a solution containing 50 grams sodium acetate in 600 mL water. A purple solid (3 grams) was obtained.

(B) Reaction of naphthalic anhydride dye with ethylene diamine

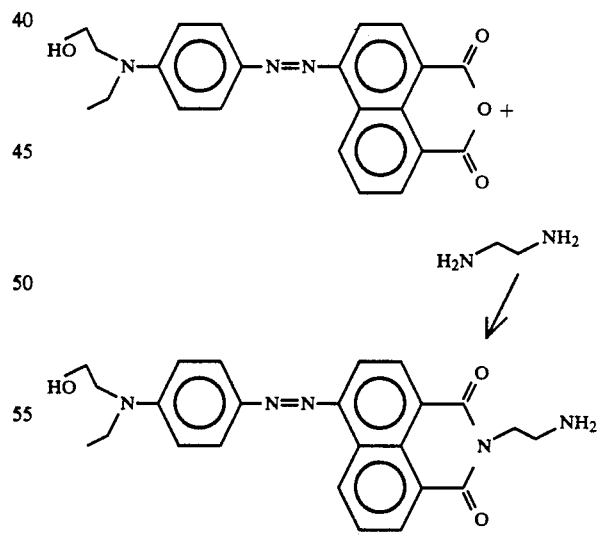

The naphthalic anhydride dye (synthesized in 32 (A)) (0.11 gram) was added to 30 mL ethanol. The slurry was heated on a hot plate to reflux and 0.5 mL ethylene diamine was added. The solution was immediately removed from the hot placte and cooled to room temperature. The desired product (0.10 gram) was obtained as a reddish powder.

EXAMPLE 33

This example described the synthesis of a functionalized azomethine nonlineaphore.

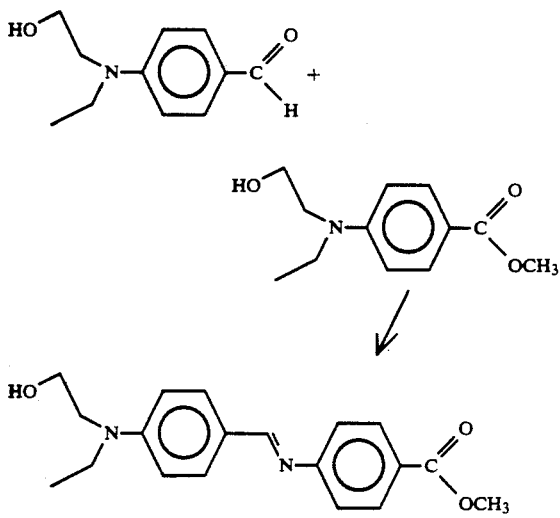

Mthyl p-aminobenzoate (0.97 grams, 0.00477 mol), 4-[N-ethyl-N-(2'-hydroxyethyl)amino]benzaldehyde (1.24 grams, 0.00477 mol) and a catalytically effective amount of p-toluenesulfonic acid were added to 50 mL toluene. The solution was refluxed for two hours. Upon cooling, a brown oily product separated. The toluene was decanted and the oily product was dissolved in ethanol. The desired product crystallized out and was obtained as a yellow solid (1 gram).

Various modifications and alterations of this invention will become apparent to those skilled in the art without departing from the scope and spirit of this invention, and it should be understood that this invention is not to be unduly limited to the illustrative embodiments set forth herein.

We claim:

1. An NLO-active composition having the formula:

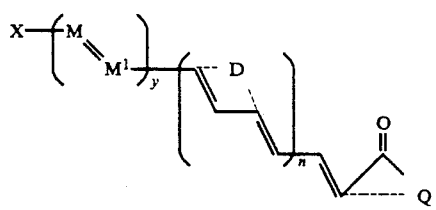

wherein:
X is

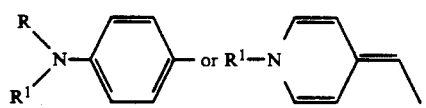

R and $R^1$ are independently an alkyl group having 1 to 10 carbon atoms, an alkyl group having 1 to 10 carbon atoms terminated with a group having an active hydrogen, R and $R^1$ taken together with a nitrogen atom form a heterocyclic ring containing five or six atoms in the ring, or R and $R^1$ taken together with a nitrogen atom form a heterocyclic ring containing five or six atoms in the ring substituted with an alkyl group substituted with an active hydrogen;

y is 0 to 2;

M and $M^1$ are independently an olefinic carbon atom or a nitrogen atom;

D is carbon atoms or heteroatoms necessary to form a 5- or 6-membered ring, wherein the heteroatoms are selected from the group consisting of nitrogen, oxygen, or sulfur;

n is 0 or 1; and

Q ia the non-metallic atoms necessary to form an indandione ring, an isoxazolone ring, a 2,4,6-triketohexahydropyrimidine ring, or a 2-thio-4-thiazolidinone (rhodanine) ring.

2. The NLO-active composition according to claim 1 wherein Q is the non-metallic atoms necessary to form a heterocyclic nucleus containing 5 or 6 atoms in the heterocyclic nucleus, having at least two heteroatoms, such that one heteroatom is nitrogen and the other heteroatoms are selected from the group consisting of nitrogen, oxygen, and sulfur atom.

3. The NLO-active composition according to claim 2, wherein Q is the non-metallic atoms necessary to complete a heterocyclic nucleus selected from the group consisting of rhodanine, isoxazolone, barbituric acid, thiobarbituric acid structural units.

4. The NLO-active composition according to claim 1, wherein the reactivity of the functional groups at the acceptor and donor ends differs from one another and the functional groups are selected from the group consisting of primary hydroxyl groups, secondary hydroxyl groups, primary amino groups, secondary amino groups, ester groups and acid groups.

5. The NLO active compositions according to claim 4, wherein the functional group at either the acceptor end or the donor end of the functionalized merocyanine dye is a hydroxyl group and the functional group at the other end is a hydroxyl group.

6. The NLO active compositions according to claim 4, wherein the functional group at either the acceptor end or the donor end of the functionalized merocyanine dye is a amino group and the functional group at the other end is a hydroxyl group.

7. The NLO-active composition according to claim 1 wherein the composition has a di-functional group at one end and an acrylate, methacrylate, acrylamide or methacrylamide group at the other end, wherein wherein the NLO-active composition has a second order nonlinear susceptibility.

8. The nonlineaphore according to claim 7, wherein the di-functional group contains at least two of a primary or secondary hydroxyl group.

9. The NLO-active composition according to claim 1 wherein the composition has a donor end and an acceptor end and a different functional group is at each end, wherein the functional group is selected from the group consisting of a hydroxyl group, an amino group, an ester group and an acid group, and further the NLO-active composition has a second order nonlinear susceptibility.

10. A nonlineaphore having the formula:

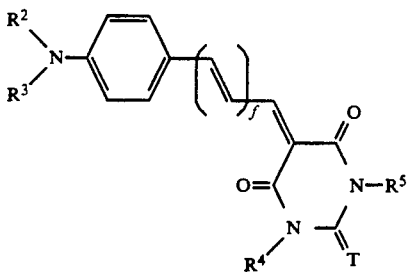

wherein:

T is sulfur or oxygen;

f is 0 or 1;

$R^2$ and $R^3$ are independently an alkyl or an aromatic group having 1 to 10 carbon atoms, an alkyl or aromatic group substituted with a group having 1 to 10 carbon atoms and substituted with an active hydrogen, $R^2$ and $R^3$ taken together form a heterocyclic ring containing 5 or 6 atoms in the ring, or $R^2$ and $R^3$ taken together form a heterocyclic ring containing 5 or 6 atoms in the ring substituted with an alkyl group substituted with an active hydrogen;

$R^4$ is a substituted phenyl, fluorenyl, or stibenyl group, wherein the substituents are electron withdrawing groups; and $R^5$ is independently an alkyl or an aromatic group, having 1 to 10 carbon atoms or an alkyl or aromatic group, having 1 to 10 carbon atoms bearing a group substituted with an active hydrogen, or $R^4$.

11. A nonlineaphore having the formula:

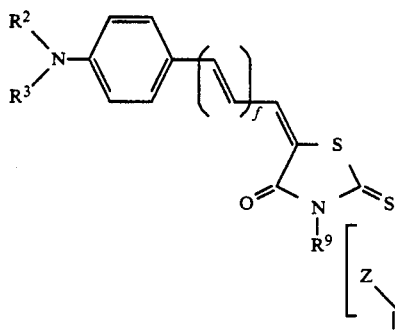

wherein:

f is 0 or 1;

$R^2$ and $R^3$ are independently an alkyl or an aromatic group having 1 to 10 carbon atoms, an alkyl or aromatic group having 1 to 10 carbon atoms and substituted with a group with an active hydrogen, $R^2$ and $R^3$ taken together form a heterocyclic ring containing 5 or 6 atoms in the ring, or $R^2$ and $R^3$ taken together form a heterocyclic ring containing 5 or 6 atoms in the ring substituted with an alkyl group substituted with an active hydrogen; and $R^9$ is independently an alkyl or an aromatic group having 1 to 10 carbon atoms, an alkyl or aromatic group having 1 to 10 carbon atoms and substituted with a group with an active hydrogen, or an alkyl group having 1 to 6 carbon atoms, substituted with an ester group or an amino group.

12. A nonlineaphore having the formula:

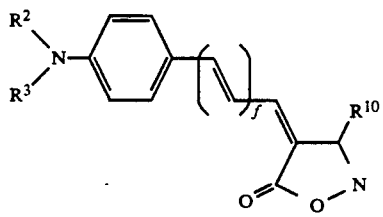

wherein:

f is 0 or 1;

$R^2$ and $R^3$ are independently an alkyl or an aromatic group having 1 to 10 carbon atoms, an alkyl or aromatic group having 1 to 10 carbon atoms and substituted with a group with an active hydrogen, $R^2$ and $R^3$ taken together form a heterocyclic ring containing 5 or 6 atoms in the, or $R^2$ and $R^3$ taken together form a heterocyclic ring containing 5 or 6 atoms in the substituted with an alkyl group substituted with an active hydrogen; and $R^{10}$ is a substituted alkyl, having 1 to 6 carbon atoms, or a substituted aromatic group having 5 or 6 carbon atoms, wherein the substituents are halogens or groups substituted with an active hydrogen.

13. A nonlineaphore derivatized from a merocyanine dye with acrylates, methacrylates, acrylamides or methacrylamides groups, said nonlineaphore having second order nonlinear susceptibilities having the formula:

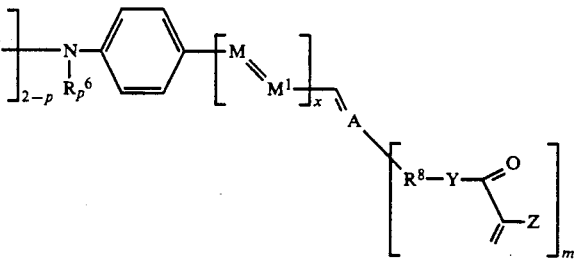

wherein:

Z is —$CH_3$ or a hydrogen atom;

p is 1 or 2;

Y is oxygen or nitrogen;

$R^6$ is a hydrogen or an alkyl having 1 to 10 carbon atoms;

$R^7$ and $R^8$ are independently an alkylene having 1 to 10 carbon atoms;

x is 0 to 2;

m is 0 to 2;

M and $M^1$ are independently an olefinic carbon atom or a nitrogen atom; and

A is any electron group or an indandione ring, an isoxazolone ring, a 2,4,6-triketohexahydropyrimidine ring, or a 2-thio-4-thiazolidinone (rhodanine) ring.

14. A nonlineaphore according to claim 10 represented by

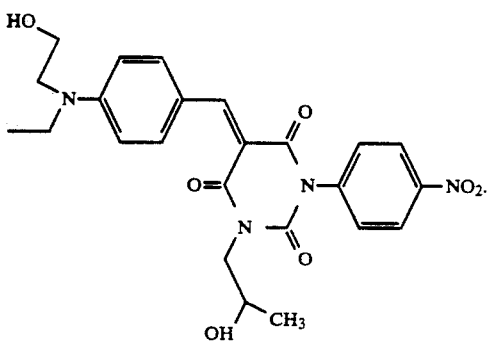

15. A nonlineaphore according to claim 10 represented by

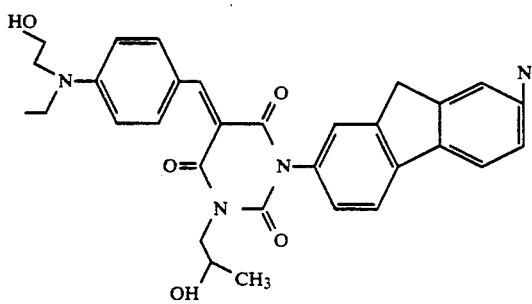

16. A nonlineaphore according to claim 10 represented by

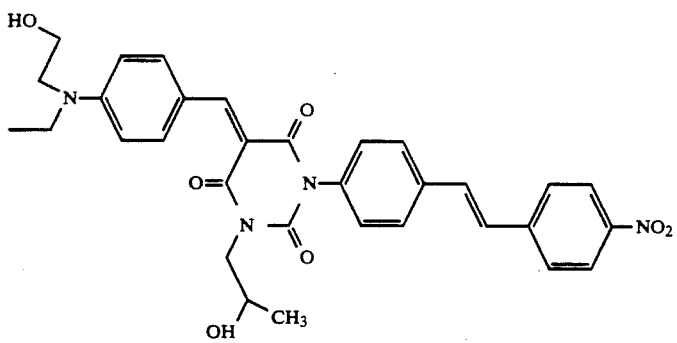

17. The nonlineaphore according to claim 13, wherein A is a heterocyclic nucleus containing 5 or 6 atoms, such that at least 3 of the atoms are carbon atoms, 1 of the atoms is a nitrogen atom, and 1 of the atoms is selected from the group consisting of a nitrogen atom, an oxygen atom, or a sulfur atom.

18. A nonlineaphore according to claim 13 represented by

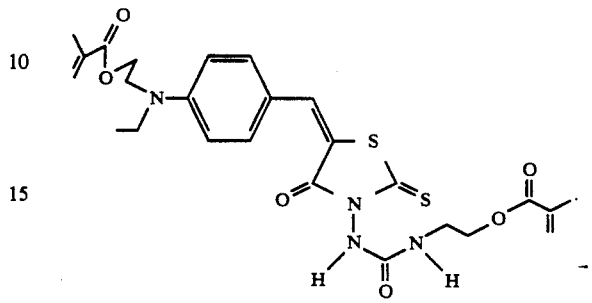

19. A nonlineaphore according to claim 13 represented by

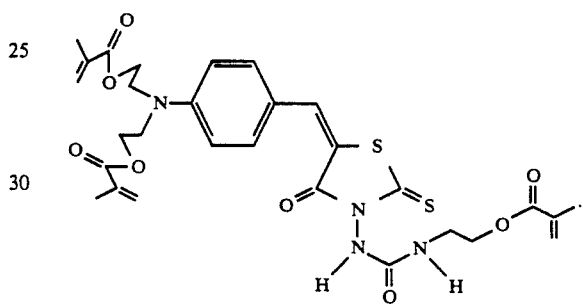

20. A nonlineaphore according to claim 13 represented by

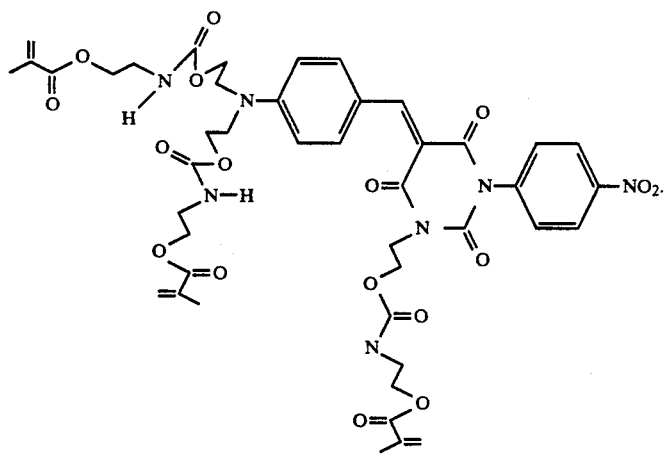
21. A nonlineaphore according to claim 13 represented by
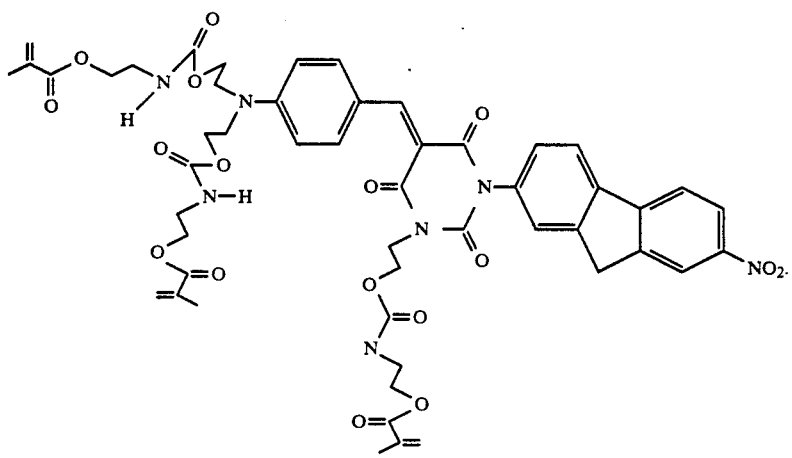
22. A nonlineaphore according to claim 13 represented by
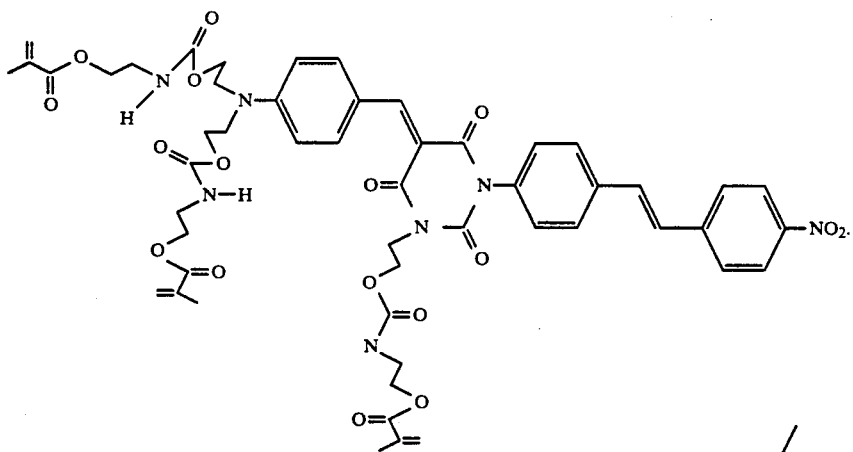
23. A nonlineaphore according to claim 11 represented by
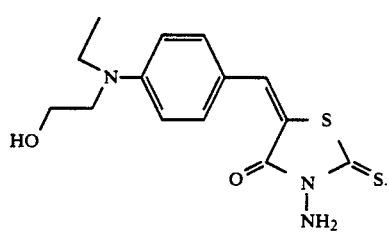
* * * * *

UNITED STATES PATENT AND TRADEMARK OFFICE
CERTIFICATE OF CORRECTION

PATENT NO. : 5,256,784
DATED : October 26, 1993
INVENTOR(S) : Francis et al.

It is certified that error appears in the above-identified patent and that said Letters Patent is hereby corrected as shown below:

Col. 3, line 28, Replace "instability" with —stability—

Col. 4, line 34, "4,60dihydroxy..." should be —4,6-dihydroxy...—

Col. 23, line 34, "N-(2-hydroxyethyl)..." should be —N-(2'-hydroxyethyl)...—

Col. 28, line 49, "reactionproduct" should be two words

Col. 35, formula for Ex. 22, One of the "O bonds" should be an S bond

Col. 41, line 52, Replace "hours" with —hour—

Col. 45, line 27, Replace "Mthyl" with —Methyl—

Col. 46, line 47, Replace "a" with —an—

Col. 46, line 54, Delete "wherein"

Col. 48, line 28, After "the" insert —ring—

Col. 48, line 30, After "the" insert —ring—

Signed and Sealed this

Fourth Day of April, 1995

*Attest:*

BRUCE LEHMAN

*Attesting Officer*  *Commissioner of Patents and Trademarks*